(12) United States Patent
Berzinis et al.

(10) Patent No.: US 10,252,221 B2
(45) Date of Patent: *Apr. 9, 2019

(54) POROUS ASYMMETRIC POLYPHENYLENE ETHER MEMBRANES AND ASSOCIATED SEPARATION MODULES AND METHODS

(71) Applicant: SABIC GLOBAL TECHNOLOGIES B.V., Bergen op Zoom (NL)

(72) Inventors: Albin Peter Berzinis, Delmar, NY (US); Pooja Bajaj, Schenectady, NY (US); Rachel Elizabeth Halbfinger, Glenville, NY (US); Matias Bikel, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 144 days.

This patent is subject to a terminal disclaimer.

(21) Appl. No.: 15/302,323

(22) PCT Filed: May 1, 2015

(86) PCT No.: PCT/US2015/028831
§ 371 (c)(1),
(2) Date: Oct. 7, 2016

(87) PCT Pub. No.: WO2015/168584
PCT Pub. Date: Nov. 5, 2015

(65) Prior Publication Data
US 2017/0021310 A1    Jan. 26, 2017

Related U.S. Application Data

(60) Provisional application No. 61/987,389, filed on May 1, 2014.

(51) Int. Cl.
*A61M 1/16*    (2006.01)
*C02F 1/44*    (2006.01)
(Continued)

(52) U.S. Cl.
CPC ............ *B01D 69/02* (2013.01); *A61M 1/1621* (2014.02); *B01D 61/14* (2013.01); *B01D 61/145* (2013.01);
(Continued)

(58) Field of Classification Search
None
See application file for complete search history.

(56) References Cited

U.S. PATENT DOCUMENTS 3,446,856 A    3/1969    Hamilton
3,522,326 A    7/1970    Bostick et al.
(Continued)

FOREIGN PATENT DOCUMENTS

CN    103007787 A    4/2013
CN    103170259 B    12/2014
(Continued)

OTHER PUBLICATIONS

Final Office Action for U.S. Appl. No. 15/356,836 dated Apr. 20, 2018, 22 pages.
(Continued)

*Primary Examiner* — Krishnan S Menon
(74) *Attorney, Agent, or Firm* — Cantor Colburn LLP

(57) ABSTRACT

A porous asymmetric membrane comprises a hydrophobic polymer comprising a poly(phenylene ether) or poly(phenylene ether) copolymer; and a polymer additive. A separation module can be fabricated from the porous asymmetric membrane. A method of forming the porous asymmetric membrane comprises: dissolving a hydrophobic polymer comprising a poly(phenylene ether) or poly(phenylene ether) copolymer and, a polymer additive in a water-miscible polar aprotic solvent to form a porous asymmetric membrane-forming composition; and phase-inverting the porous asymmetric membrane forming-composition in a
(Continued)

first non-solvent composition to form the porous asymmetric membrane. The polymer additive comprises hydrophilic functional groups, copolymerized hydrophilic monomers, or blocks of hydrophilic monomer repeat units. For example, the polymer additive can comprise a hydrophilic polymer or amphiphilic polymer. The porous asymmetric membrane can be a flat membrane or hollow fiber.

20 Claims, 8 Drawing Sheets

(51) Int. Cl.
| C07K 1/34 | (2006.01) |
| B01D 61/14 | (2006.01) |
| B01D 61/36 | (2006.01) |
| B01D 63/02 | (2006.01) |
| B01D 67/00 | (2006.01) |
| B01D 69/02 | (2006.01) |
| B01D 69/06 | (2006.01) |
| B01D 69/08 | (2006.01) |
| B01D 69/12 | (2006.01) |
| B01D 71/28 | (2006.01) |
| B01D 71/52 | (2006.01) |
| B01D 71/56 | (2006.01) |
| B01D 71/76 | (2006.01) |
| B01D 71/78 | (2006.01) |
| B01D 71/80 | (2006.01) |
| C08B 37/00 | (2006.01) |
| C02F 101/32 | (2006.01) |

(52) U.S. Cl.
CPC ........... *B01D 61/364* (2013.01); *B01D 63/02* (2013.01); *B01D 67/0016* (2013.01); *B01D 67/0095* (2013.01); *B01D 69/06* (2013.01); *B01D 69/08* (2013.01); *B01D 69/088* (2013.01); *B01D 69/125* (2013.01); *B01D 71/28* (2013.01); *B01D 71/52* (2013.01); *B01D 71/56* (2013.01); *B01D 71/76* (2013.01); *B01D 71/78* (2013.01); *B01D 71/80* (2013.01); *C02F 1/441* (2013.01); *C07K 1/34* (2013.01); *C08B 37/0003* (2013.01); *B01D 2323/02* (2013.01); *B01D 2323/04* (2013.01); *B01D 2323/22* (2013.01); *B01D 2323/36* (2013.01); *B01D 2323/40* (2013.01); *B01D 2325/022* (2013.01); *B01D 2325/34* (2013.01); *B01D 2325/36* (2013.01); *B01D 2325/38* (2013.01); *C02F 2101/32* (2013.01); *Y02W 10/37* (2015.05)

(56) References Cited

U.S. PATENT DOCUMENTS

| 3,703,564 A | 11/1972 | White |
| 3,770,699 A | 11/1973 | White |
| 3,970,640 A | 7/1976 | Yonemitsu et al. |
| 4,201,880 A | 5/1980 | Van Sorge |
| 4,277,344 A | 7/1981 | Cadotte |
| 4,278,777 A | 7/1981 | Jakabhazy et al. |
| 4,338,421 A | 7/1982 | Maruyama et al. |
| 4,454,284 A | 6/1984 | Ueno et al. |
| 4,622,206 A | 11/1986 | Torgeson |
| 4,882,168 A | 11/1989 | Casey et al. |
| 4,933,081 A | 6/1990 | Sasaki et al. |
| 4,944,775 A | 7/1990 | Hayes |
| 5,069,793 A | 12/1991 | Kaschemekat et al. |
| 5,118,327 A | 6/1992 | Nelson et al. |
| 5,128,421 A | 7/1992 | Ohmura et al. |
| 5,132,363 A | 7/1992 | Furuta et al. |
| 5,159,027 A | 10/1992 | Kanayama et al. |
| 5,209,849 A | 5/1993 | Hu et al. |
| 5,282,964 A | 2/1994 | Young et al. |
| 5,385,976 A | 1/1995 | Furuta et al. |
| 5,480,552 A | 1/1996 | Soltys et al. |
| 5,527,467 A | 6/1996 | Oftshun et al. |
| 5,643,968 A | 7/1997 | Andreola et al. |
| 5,795,920 A | 8/1998 | Kang et al. |
| 5,834,583 A | 11/1998 | Hancock et al. |
| 6,294,499 B1 | 9/2001 | Watson et al. |
| 6,437,084 B1 | 8/2002 | Birsak et al. |
| 6,472,499 B1 | 10/2002 | Braat et al. |
| 7,166,148 B2 | 1/2007 | Lyons et al. |
| 7,208,438 B2 | 4/2007 | Ingelbrecht et al. |
| 8,222,342 B2 | 7/2012 | Weber et al. |
| 8,287,735 B2 | 10/2012 | Hanemaaijer et al. |
| 8,302,781 B2 | 11/2012 | Wechs et al. |
| 8,505,745 B2 | 8/2013 | Mayes et al. |
| 8,602,221 B2 | 12/2013 | Mizomoto et al. |
| 8,727,136 B2 | 5/2014 | Ansorge et al. |
| 8,741,600 B2 | 6/2014 | Yamaguchi et al. |
| 9,133,338 B2 | 9/2015 | Yang et al. |
| 2004/0145127 A1 | 7/2004 | Pinto |
| 2004/0149127 A1 | 8/2004 | Lyons et al. |
| 2004/0231663 A1 | 11/2004 | Carter et al. |
| 2005/0218057 A1 | 10/2005 | Ngee |
| 2006/0076884 A1 | 4/2006 | Ahn |
| 2006/0076885 A1 | 4/2006 | Kim et al. |
| 2006/0137522 A1 | 6/2006 | Nishimura et al. |
| 2007/0068871 A1 | 3/2007 | Flynn |
| 2007/0202374 A1 | 8/2007 | Bridges et al. |
| 2007/0238832 A1 | 10/2007 | Borade et al. |
| 2008/0076884 A1 | 3/2008 | Yeager et al. |
| 2008/0076885 A1 | 3/2008 | Yeager et al. |
| 2008/0085989 A1 | 4/2008 | Yeager et al. |
| 2008/0142429 A1 | 6/2008 | Zhang et al. |
| 2008/0203012 A1 | 8/2008 | Yeager et al. |
| 2008/0207822 A1 | 8/2008 | Yeager et al. |
| 2008/0312349 A1 | 12/2008 | Yeager et al. |
| 2009/0018303 A1 | 1/2009 | Onizuka et al. |
| 2010/0244306 A1 | 9/2010 | Tang |
| 2012/0100904 A1 | 5/2012 | Morita et al. |
| 2012/0103904 A1 | 5/2012 | Morita et al. |
| 2012/0277347 A1 | 11/2012 | Bedner et al. |
| 2012/0305486 A1 | 12/2012 | Storr et al. |
| 2013/0220924 A1 | 8/2013 | Maeda |
| 2016/0008528 A1 | 1/2016 | Roy et al. |
| 2016/0021191 A1 | 1/2016 | Wang et al. |
| 2016/0022892 A1 | 1/2016 | Eifler et al. |
| 2016/0079616 A1 | 3/2016 | Lee et al. |
| 2017/0282131 A1 | 10/2017 | Berzinis et al. |
| 2018/0079863 A1 | 3/2018 | Ghanta |

FOREIGN PATENT DOCUMENTS

| EP | 0216633 | 4/1987 |
| EP | 0568045 A1 | 11/1993 |
| EP | 0083489 B1 | 4/1999 |
| EP | 1918019 A1 | 5/2008 |
| EP | 2535101 A1 | 12/2012 |
| JP | S42004276 B | 2/1964 |
| JP | S46002837 B | 10/1967 |
| JP | S46006542 | 12/1971 |
| JP | S60114323 A | 6/1985 |
| JP | S62057915 | 3/1987 |
| JP | S62071503 A | 4/1987 |
| JP | S62152507 A | 7/1987 |
| JP | S63100916 A | 5/1988 |
| JP | S63128021 A | 5/1988 |
| JP | S63197502 | 8/1988 |
| JP | S63218231 A | 9/1988 |
| JP | S63230173 A | 9/1988 |
| JP | H03065227 A | 3/1991 |
| JP | H04011927 | 1/1992 |
| JP | H08143699 A | 6/1996 |
| JP | S64030621 | 2/1999 |
| JP | H11156165 A | 6/1999 |
| JP | H11322921 A | 11/1999 |
| JP | 2000246064 A | 9/2000 |

(56) References Cited

FOREIGN PATENT DOCUMENTS

| JP | 2004231743 | A | 8/2004 |
|---|---|---|---|
| JP | 2005262211 | A | 9/2005 |
| JP | 2013013838 | A | 1/2013 |
| JP | 2014205761 | A | 10/2014 |
| WO | 0240140 | A1 | 5/2002 |
| WO | 03000389 | A2 | 1/2003 |
| WO | 2004056459 | A1 | 7/2004 |
| WO | 2005107929 | A2 | 11/2005 |
| WO | 2008103599 | A2 | 8/2008 |
| WO | 2012008837 | A2 | 1/2012 |
| WO | 2013131848 | A1 | 9/2013 |
| WO | 2014195234 | A1 | 12/2014 |
| WO | 2015168392 | A1 | 11/2015 |
| WO | 2015168409 | A1 | 11/2015 |
| WO | 2015168414 | A1 | 11/2015 |
| WO | 2015168423 | A1 | 11/2015 |
| WO | 2015168592 | A1 | 11/2015 |
| WO | 2015168418 | A1 | 11/2016 |
| WO | 2016178835 | A1 | 11/2016 |

OTHER PUBLICATIONS

Machine Translation for JPH08143699 obtained from Espacenet on Jan. 12, 2018, 10 pages; (https://worldwide.espacenet.com/publicationDetails/biblio?II=0&ND=3&adjacent=true&locale=en_EP&FT=D&date=19960604&CC=JP&NR=H08143699A&KC=A#).
Machine Translation for JPS4665420A obtained from J-Plat Pat on Jan. 8, 2018, 14 pages; (https://www4.j-platpat.inpit.go.jp/cgi-bin/tran_web_cgi_ejje?u=http://www4.j-platpat.inpit.go.jp/eng/translation/201804240506474023768556212174105 6C2CF07F06D8BF80DAC7BA11D51D95A0).
Machine Translation for JPS62152507A obtained from Espacenet on Jan. 12, 2018, 11 pages; (https://worldwide.espacenet.com/publicationDetails/biblio?II=0&ND=3&adjacent=true&locale=en_EP&FT=D&date=19870707&CC=JP&NR=S62152507A&KC=A#).
Machine Translation for JPH011322921A.
Advisory Action dated Aug. 8, 2017 for U.S. Appl. No. 15/356,836; 4 Pages.
International Preliminary Report on Patentability for International Application No. PCT/US2016/028951; Date of Filing: Apr. 22, 2016; dated Aug, 7, 2017; 57 pages.
Machine Translation for JPH08143699.
Machine Translation for JPS46006542.
Machine Translation for JPS62152507A.
Non-Final Office Action dated Jan. 4, 2018 for U.S. Appl. No. 15/536,836; 11 Pages.
U.S. Notice of Allowance, U.S. Appl. No. 15/356,854, dated Aug. 16, 2017, 16 pages.
Written Opnion of the International Searching Authority for International Application No. PCT/US2016/028951; Date of Filing: Apr. 22, 2016; dated Apr. 11, 2017; 10 pages.
Non-Final Office Action for U.S. Appl. No. 15/303,556; dated May 3, 2018; 30 pages.
Restriction Requirement for U.S. Appl. No. 15/303,058; dated May 1, 2018; 8 pages.
Restriction Requirement for U.S. Appl. No. 15/303,061; dated May 4, 2018; 8 pages.
Restriction Requirement for U.S. Appl. No. 15/303,561; dated Apr. 27, 2018; 10 pages.
Restriction Response for U.S. Appl. No. 15/302,276; dated Apr. 23, 2018: 8 pages.
CN 103170259; Machine Translation; Date of Publication: Dec. 10, 2014; 10 pages.
Final Office Action dated Jun. 7, 2017; U.S. Appl. No. 15/356,836; filed Nov. 21, 2016; 16 pages.
International Search Report for International Application No. PCT/US2016/028951; International Filing Date Apr. 22, 2016; dated Jul. 29, 2016; 7 pages.
International Search Report for International Application No. PCT/US2017/022061; Date of Filing: Mar. 13, 2017; dated Jul. 4, 2017; 6 pages.
International Search Report for International Application No. PCT/US2017/022088; Date of Filing: Mar. 13, 2017; dated Jun. 28, 2017; 6 pages.
JP S60114323; Machine Translation; Date of Publication: Jun. 20, 1985; 8 pages.
Loh et al.; "Fabrication of high performance polyethersulfone UF hollow fiber membranes using amphiphilic Pluronic block copolymers as pore-forming additives"; J. Membr. Sci., vol. 380; 2011; 114-123.
Non-Final Office Action dated Feb. 16, 2017; U.S. Appl. No. 15/356,836, filed Nov. 21, 2016; 24 pages.
Non-Final Office Action dated Mar. 6, 2017; U.S. Appl. No. 15/356,854, filed Nov. 21, 2016; 28 pages.
Susanto et al.; "Characteristics, performance and stability of polyethersulfone ultrafiltration membranes prepared by phase separation method using different macromolecular additives"; J. Membr. Sci., vol. 327; 2009; p. 125-35.
U.S. Appl. No. 15/356,836 to Berzinis; filed Nov. 21, 2016; 29 pages.
U.S. Appl. No. 15/356,854 to Berzinis; filed Nov. 21, 2016; 38 pages.
U.S. Appl. No. 62/155,593 to Berzinis; filed May 1, 2015; 36 pages.
Written Opinion of the International Search Report for International Application No. PCT/US2016/028951; International Filing Date Apr. 22, 2016; dated Jul. 29, 2016; 9 pages.
Written Opinion of the International Searching Authority for International Application No. PCT/US2017/022061; Date of Filing: Mar. 13, 2017; dated Jul. 4, 2017; 9 pages.
Written Opinion of the International Searching Authority for International Application No. PCT/US2017/022088; Date of Filing: Mar. 13, 2017; dated Jun. 28, 2017; 8 pages.
Asatekin et al.; "Anti-fouling ultrafiltration membranes containing polyacrylonitrile-graft-poly(ethylene oxide) comb copolymer additives"; Journal of Membrane Science 298 (2007) pp. 136-146.
ATRP Solutions; 2011 Catalog; 9 pages.
Baker; "Membranes and Modules"; Membrane Technology & Applications, Third Edition; 2012 John Wiley & Sons; pp. 97-178.
Bernardo et al.; "Membrane Gas Separation: A Review/State of the Art"; Ind. Eng. Chem. Res. 2009, 48, pp. 4638-4663.
Chung et al.; "Formation of ultrathin high-performance polyethersulfone hollow-fiber membranes"; Journal of Membrane Science 133 (1997) pp. 161-175.
Cooper et al.; "Preparation and Properties of Poly(arylene oxide) Copolymers"; Advances in Chemistry; American Chemical Society; 1973; pp. 230-257.
Cooper et al.; "Preparation and Properties of Polyarylene Oxide Copolymers"; 1973; pp. 551-556.
Dongliang et al.; "Polyethersulfone hollow fiber gas separation membranes prepared from NMP/alcohol solvent systems"; Journal of Membrane Science; 115; 1996, pp. 85-108.
International Search Report for International Application No. PCT/US2015/028546, International Filing Date Apr. 30, 2015, dated Aug. 4, 2015, 5 pages.
International Search Report for International Application No. PCT/US2015/028831, International Filing Date May 1, 2015, dated Jul. 30, 2015, 5 pages.
Kang et al.; "Protein antifouling mechanisms of PAN UF membranes incorporating PAN-g-PEO additive"; Journal of Membrane Science 296 (2007) pp. 42-50.
Kim et al.; "Ultrafiltration membranes prepared from blends of polyethersulfone and poly(1-vinylpyrrolidone-co-styrene) copolymers"; Journal of Membrane Science 262 (2005) pp. 60-68.
Liang et al.; "Synthesis and characterization of poly(phenylene oxide) graft copolymers by atom transfer radical polymerizations"; European Polymer Journal 45 (2009) pp. 2348-2357.
Petersen; "Composite reverse osmosis and nanofiltration membranes"; Journal of Membrane Science, 83 (1993) pp. 81-150.
Semsarzadeh et al.; "Synthesis and Characterization of Poly(phenylene oxide)-Based Block Copolymers via Cobalt Mediated Radical Polymerization (CMRP)"; Silicon; 6, 2014, pp. 27-34.

(56) References Cited

OTHER PUBLICATIONS

Smid et al.; "The formation of asymmetric hollow fibre membranes for gas separation, using PPE of different intrinsic viscosities"; Journal of Membrane Science, 64, 1991, pp. 121-128.
Ulbricht, "Advanced functional polymer membranes", Polymer; 47; Jan. 2006; pp. 2217-2262.
Vandezande et al.; "High throughput study of phase inversion parameters for polyimide-based SRNF membranes"; Journal of Membrane Science, 330, 2009, pp. 307-318.
Wang et al.; "Highly permeable polyethersulfone hollow fiber gas separation membranes prepared using water as non-solvent additive"; Journal of Membrane Science 176 (2000) pp. 147-158.
Wang et al.; "Polyethersulfone hollow fiber gas separation membranes prepared from NMP/alcohol solvent systems"; Journal of Membrane Science 115 (1996) pp. 85-108.
Written Opinion for International Application No. PCT/US2015/028546, International Filing Date Apr. 30, 2015, dated Aug. 4, 2015.
Written Opinion for International Application No. PCT/US2015/028831, International Filing Date May 1, 2015, dated Jul. 30, 2015, 8 pages.
Yang et al.; "Tailoring pore size and pore size distribution of kidney dialysis hollow fiber membranes via dual-bath coagulation approach"; Journal of Membrane Science 290 (2007) pp. 153-163.
Yeager et al.; "Polyethers, Aromatic"; Encyclopedia of Polymer Science and Technology; vol. 11; John Wiley & Sons; 2003; pp. 64-87.
Non-Final Office Action for U.S. Appl. No. 15/303,562; dated Feb. 6, 2018.
Non Final Office Action for U.S. Appl. No. 15/303,561; dated Jul. 26, 2018; 16 pages.
Advisory Action for U.S. Appl. No. 15/356,836; dated Jul. 3, 2018; 9 Pages.
Li et al., Ed., "Water Treatment and Water Quality Control of Power Station"; China Electric Power Press; 2012; pp. 203-204.
Li et al., Ed., "Water Treatment and Water Quality Control of Power Station"; China Electric Power Press; 2012; pp. 203-204 (Original in Chinese).
Non Final Office Action for U.S. Appl. No. 15/303,061; dated Jul. 19, 2018; 53 pages.
Non-Final Office Action for U.S. Appl. No. 15/302,276; dated Jul. 19, 2018; 45 pages.
Non-Final Office Action for U.S. Appl. No. 15/303,058; dated Jul. 19, 2018; 56 pages.
Notice of Allowance for U.S. Appl. No. 15/303,562; dated Jun. 1, 2018; 25 pages.
Shi et al., Ed., "Membrane Technology Manual"; Chemical Industry Press; 2001; p. 199 (Original in Chinese).
Shi et al., Ed., "Membrane Technology Manual"; Chemical industry Press; 2001; p. 199.
Wang, Ed. "Biomedical Engineering Principles"; Science Press; 1982; p. 326 (Original in Chinese).
Wang, Ed. "Biomedical Engineering Principles"; Science Press; 1982; p. 326.
Wang, Ed., "Membrane Separation Technology and Use Thereof"; Science Press; 1994; p. 181 (Original in Chinese).
Wang, Ed., "Membrane Separation Technology and Use Thereof"; Science Press; 1994; p. 181.
Zhong et al., Ed., "Principle of Chemical Industry"; National Defense Industry Press; 2013; p. 399 (Original in Chinese).
Zhong et al., Ed., "Principle of Chemical Industry"; National Defense Industry Press; 2013; p. 399.

POROUS ASYMMETRIC POLYPHENYLENE ETHER MEMBRANES AND ASSOCIATED SEPARATION MODULES AND METHODS

CROSS REFERENCE TO RELATED APPLICATIONS

This application is a National Stage application of PCT/US2015/028831, filed May 1, 2015, which claims the benefit of U.S. Provisional Application No. 61/987,389, filed May 1, 2014, both of which are incorporated by reference in their entirety herein.

BACKGROUND OF THE INVENTION

Reverse osmosis is utilized in membrane separation process whereby a feed stock containing a solute, which has molecular or colloidal dimensions which are significantly greater than the molecular dimensions of its solvent, is depleted of the solute by being contacted with the membrane at such pressure that the solvent permeates the membrane and the solute is retained. This results in a permeate fraction which is solute-depleted and a retentate fraction which is solute-enriched. In ultrafiltration, microfiltration, ultrafiltration, and nanofiltration, pressure in excess of the osmotic pressure can be used to force the solvent through the membrane against a concentration gradient of solute.

Poly(phenylene ether)s are a class of plastics having excellent water resistance, thermal resistance, and dimensional stability. They retain their mechanical strength in hot, and/or wet environments. Therefore they can be used for the fabrication of porous asymmetric membranes useful in various separation processes, including reverse osmosis. For example, poly(phenylene ether)s can be used in processes that require repeated cleaning with hot water or steam sterilization. Nonetheless, there remains a need for a porous asymmetric membrane having improved filtration properties, including materials that will improve selectivity without adversely affecting permeation flux.

The surface of membranes fabricated from hydrophobic polymers can be made hydrophilic by blending with a polymer additive that is hydrophilic. For example, polyethersulfone can be blended with poly(N-vinylpyrrolidone), and the two polymers can be co-precipitated from solution to form a membrane. However, excess poly(N-vinylpyrrolidone) must be washed off of the membrane with water, which results in a waste of valuable material, and which produces an aqueous waste comprising the excess poly(N-vinylpyrrolidone). Moreover the hydrophilic polymer can be leached out of the membrane in membrane treatment of aqueous streams. There remains a need for a polymer additive that provides a hydrophilic surface to porous asymmetric membranes fabricated from hydrophobic polymers. The polymer additive should have hydrophilic character and yet have an affinity for the hydrophobic polymer, so that the polymer additive is not extracted by washing during fabrication or in end-use operation of the membrane.

BRIEF DESCRIPTION OF THE INVENTION

A porous asymmetric membrane comprises, consists essentially of, or consists of a hydrophobic polymer comprising, consisting essentially of, or consisting of a poly(phenylene ether) or poly(phenylene ether) copolymer; and a polymer additive. A separation module can be fabricated from the porous asymmetric membrane.

A method of forming the porous asymmetric membrane comprises: dissolving a hydrophobic polymer comprising, consisting essentially of, or consisting of a poly(phenylene ether) or poly(phenylene ether) copolymer and, a polymer additive in a water-miscible polar aprotic solvent to form a porous asymmetric membrane-forming composition; and phase-inverting the porous asymmetric membrane forming-composition in a first non-solvent composition to form the porous asymmetric membrane.

A method of making a hollow fiber by coextrusion through a spinneret comprising an annulus and a bore, comprises coextruding: a membrane-forming composition comprising a hydrophobic polymer comprising a poly(phenylene ether) or poly(phenylene ether) copolymer, and a polymer additive dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber. A hollow fiber made by the method can be fabricated into a separation module.

BRIEF DESCRIPTION OF THE DRAWINGS

Referring now to the drawings.

DETAILED DESCRIPTION OF THE INVENTION

Figure 1:
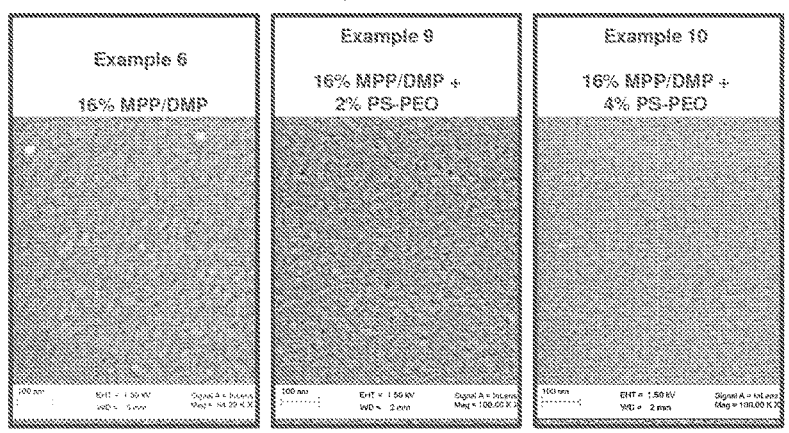
FIG. 1 depicts scanning electron microscopy (SEM) images of the porous asymmetric membrane surfaces Examples 6 and 9-10.

The inventors hereof have discovered specific polymer additives that are particularly effective in combination with hydrophobic polymers comprising poly(phenylene ether) or poly(phenylene ether) copolymer; for the manufacture of asymmetric membranes and hollow fibers used in ultrafiltration. The polymer additive can comprise hydrophilic functional groups, copolymerized hydrophilic monomers, or blocks of hydrophilic monomer repeat units. For example, the polymer additive can comprise a hydrophilic polymer or amphiphilic polymer. An amphiphilic polymer is a polymer that has both hydrophilic (water-loving, polar) and hydrophobic (water-hating, non-polar) properties.

Advantageously, use of the polymer additive in combination with a hydrophobic polymer comprising a poly(phenylene ether) or poly(phenylene ether) copolymer provides a porous asymmetric membranes having surface pore size distributions, surface pore densities, and water contact angles that make the porous asymmetric membrane suitable for use in separation modules for purification of aqueous streams by ultrafiltration. The polymer additive provides a more hydrophilic surface to porous asymmetric membranes fabricated from hydrophobic polymers comprising a poly(phenylene ether) or poly(phenylene ether) copolymer, and yet has an affinity for the poly(phenylene ether) or poly(phenylene ether) copolymer, so that it is not extracted by washing during fabrication or in end-use operation of the porous asymmetric membrane in separation modules.

The porous asymmetric membrane comprises consists essentially of, or consists of: a hydrophobic polymer comprising, consisting essentially of, or consisting of a poly(phenylene ether) or poly(phenylene ether) copolymer; and a polymer additive. In some embodiments, the hydrophobic polymer comprises a poly(phenylene ether) copolymer comprising first and second repeat units independently having the structure (I):

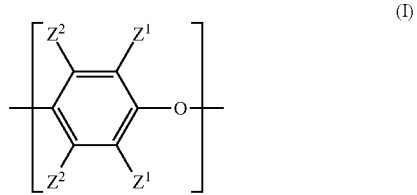

wherein each occurrence of $Z^1$ is independently halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy, wherein at least two carbon atoms separate the halogen and oxygen atoms; wherein each occurrence of $Z^2$ is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy, wherein at least two carbon atoms separate the halogen and oxygen atoms; and wherein the first and second repeat units are different.

The hydrophobic polymer can be a poly(phenylene ether) copolymer having an intrinsic viscosity greater than or equal to 0.7, 0.8, 0.9, 1.0, or 1.1 deciliters per gram, and less than or equal to 1.5, 1.4, or 1.3 deciliters per gram, when measured in chloroform at 25° C. In some embodiments, the intrinsic viscosity is 1.1 to 1.3 deciliters per gram. In some embodiments, the poly(phenylene ether) copolymer has a weight average molecular weight of 100,000 to 500,000 daltons (Da), as measured by gel permeation chromatography against polystyrene standards. Within this range, the weight average molecular weight can be greater than or equal to 150,000 or 200,000 Da and less than or equal to 400,000, 350,000, or 300,000 Da. In some embodiments, the weight average molecular weight is 100,000 to 400,000 Da, specifically 200,000 to 300,000 Da. The poly(phenylene ether) copolymer can have a polydispersity (ratio of weight average molecular weight to number average molecular weight of 3 to 12. Within this range, the polydispersity can be greater than or equal to 4 or 5 and less than or equal to 10, 9, or 8.

A method of forming the porous asymmetric membrane, comprises: dissolving a hydrophobic polymer comprising, consisting essentially of, or consisting of a poly(phenylene ether) or poly(phenylene ether) copolymer and, a polymer additive in a water-miscible polar aprotic solvent to form a porous asymmetric membrane-forming composition; and phase-inverting the porous asymmetric membrane forming-composition in a first non-solvent composition to form the porous asymmetric membrane. Any of several techniques for phase inversion can be used. For example, the phase inversion can be a dry-phase separation method in which the dissolved copolymer is precipitated by evaporation of a sufficient amount of solvent mixture to form the membrane. The phase inversion step can also be a wet-phase separation method in which the dissolved copolymer is precipitated by immersion in the first non-solvent to form the membrane. The phase inversion step can be a dry-wet phase separation method, which is a combination of the dry-phase and the wet-phase methods. The phase inversion step can be a thermally-induced separation method in which the dissolved copolymer is precipitated or coagulated by controlled cooling to form the membrane. The membrane, once formed, can be subjected to membrane conditioning or pretreatment, prior to its end-use. The conditioning or pretreatment can be thermal annealing to relieve stresses or pre-equilibration in the expected feed stream.

The porous asymmetric membrane exhibits many advantageous surface properties. The polymer additive is incorporated into the selective surface layer of the porous asymmetric membrane by the method, which advantageously reduces the water contact angle of the surface compared to a porous asymmetric membrane made from the hydrophobic polymer without the polymer additive. For example, the porous asymmetric membrane can have a water contact angle of greater than or equal to 20, 30, or 40 degrees, and less than or equal to 80, 70, or 60 degrees. In some embodiments, the porous asymmetric membrane has a water contact angle of 40 to 80 degrees. The porous asymmetric membrane made by the method can have a mean surface pore size distribution on the selective layer of greater than or equal to 1, 5, 10 nanometers (nm) and less than or equal to 100, 50, or 20 nm±1, 2, 5, or 10 nm. The porous asymmetric membrane made by the method can also have a surface pore density of greater than or equal to 100, 200, or 400 pores per $\mu m^2$ and less than or equal to 4,000, 2,400, or 1,200 pores per $\mu m^2$.

The method is also applicable to making hollow fibers by coextrusion of a dope solution and a bore fluid, in which the membrane-forming composition is the dope solution and the first non-solvent composition is the bore fluid. Thus in some embodiments, a method of making a hollow fiber by coextrusion through a spinneret comprising an annulus and a bore, comprises coextruding coextruding: a membrane-forming composition comprising a hydrophobic polymer comprising a poly(phenylene ether) or poly(phenylene ether) copolymer, and a polymer additive dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber.

A hollow fiber is made by coextruding through a spinneret comprising an annulus and a bore: a membrane-forming composition comprising a hydrophobic polymer comprising a poly(phenylene ether) or poly(phenylene ether) copolymer, and a polymer additive dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber. The hollow fibers can be used in various separation modules, for example those described herein.

The configuration of the porous asymmetric membrane made by the method can be sheet, disc, spiral wound, plate and frame, hollow fiber, capillary, or tubular. Outside-in and inside-out separations are applicable to hollow fiber membranes, capillary membranes, and tubular membranes, each having an inner and outer surface in contact with the feed and retentate or the permeate.

The porous asymmetric membrane made by the method can be a porous hollow fiber. The wall thickness of the hollow fiber can be 20 to 100 micrometers (μm). Within this range, the wall thickness can be greater than 30 and less than or equal to 80, 60, 40 or 35 μm. In another embodiment the fiber diameter can be 50 to 3000 a μm, specifically 100 to 2000 μm. The membrane can comprise a substantially non-porous surface layer, and the non-porous surface layer can be on the inside surface of the hollow fiber. A separation module can comprise bundles of porous hollow fibers. In some embodiments, the fiber bundle comprises 10 to 10,000 porous hollow fibers. The hollow fibers can be bundled longitudinally, potted in a curable resin on both ends, and encased in a pressure vessel to form the hollow fiber module. Hollow fiber modules can be mounted vertically or horizontally.

The porous asymmetric membranes can be fabricated into separation modules designed for purification of various aqueous, non-aqueous (e.g., hydrocarbon), or gaseous streams. Thus in some embodiments, a separation module comprises the porous asymmetric membrane comprising, consisting essentially of, or consisting of: a hydrophobic polymer comprising, consisting essentially of, or consisting of a poly(phenylene ether) or poly(phenylene ether) copolymer and a polymer additive. The separation module can be designed for dead-end separation, cross-flow separation, inside-out separation, or outside-in separation.

Depending upon porous asymmetric membrane surface pore size distribution and pore density, and the end-use, the separation module fabricated from the porous asymmetric membrane made by the method can be a media filtration module, a microfiltration module, an ultrafiltration module, a nanofiltration module, or a reverse osmosis module. The separation module fabricated from the porous asymmetric membrane made by the method can also be a membrane contactors module, a pervaporation module, a dialysis module, an osmosis module, an electrodialysis module, a membrane electrolysis module, an electrophoresis module, or a membrane distillation module. For media filtration, the surface pore size can be about 100 to about 1,000 micrometers. For microfiltration, the surface pore size can be about 0.03 to about 10 micrometers. For ultrafiltration, the surface pore size can be about 0.002 to 0.1 micrometers. For nanofiltration, the surface pore size can be about 0.001 to about 0.002 micrometers. The porous asymmetric membranes described herein are surprisingly well suited for ultrafiltration and nanofiltration. In some embodiments, the porous asymmetric membrane has a surface pore size of 0.001 to 0.05 micrometers (μm), specifically 0.005 to 0.01 μm.

The molecular weight cut off (MWCO) of a membrane is the lowest molecular weight solute in which 90 weight percent (wt %) or greater of the solute is retained by the membrane. The porous asymmetric membranes made by the method can have a MWCO of 500 to 40,000 daltons (Da), specifically 1,000 to 10,000 Da, more specifically 2,000 to 8,000 Da, or still more specifically 3,000 to 7,000 Da. Furthermore, any of the foregoing MWCO ranges can be present in combination with a desirable permeate flux, such as clean water permeate flux (CWF). For example, the permeate flux can be 1 to 200, specifically 2 to 100, more specifically 4 to 50 L/(h·m$^2$·bar), wherein L is liters and m$^2$ is square meters. The porous asymmetric membranes made by the method can also provide a CWF of about 10 to about 80 L/(h·m$^2$·bar), about 20 to about 80 L/(h·m$^2$·bar), or about 40 to about 60 L/(h·m$^2$·bar). Flux across the membrane is driven by the osmotic or absolute pressure differential across the membrane, referred to herein as the trans-membrane pressure (TMP). The trans-membrane pressure can be 1 to 500 kilopascals (kPa), specifically 2 to 400 kPa, and more specifically 4 to 300 kPa.

The porous asymmetric membranes disclosed herein are useful for treatment of aqueous streams. Depending upon pore size and porous asymmetric membrane configuration, the membranes can be used to remove suspended matter, particulate matter, sands, silt, clays, cysts, algae, microorganisms, bacteria, viruses, colloidal matter, synthetic and naturally occurring macromolecules, dissolved organic compounds, salts, or a combination comprising at least one of the foregoing. Thus, the porous asymmetric membranes disclosed herein can be used in wastewater treatment, water purification, food processing, the dairy industry, biotechnology, pharmaceuticals, and healthcare.

The pharmaceutical or biotechnological processes or food processing applications can include, for instance, the removal of salts and/or low molecular weight byproducts from solutions (product streams) by way of dialysis or increasing the concentration of a product having a molecular weight above the cut-off of the membrane in a solution by way of ultrafiltration, such solutions including human blood, animal blood, lymph fluids, or microbial or cellular suspensions (e.g. bacterial, plant cells, animal blood or lymph fluids, or microbial or cellular suspensions). Specific applications include the concentration and purification of peptides in blood plasma; hemofiltration; hemodialysis; hemodiafiltration; renal dialysis; and enzyme recovery. Food processing can involve solutions such as meat products and by-products, plant extracts, suspensions of algae or fungi, vegetable food and beverages containing particles such as pulp, milk processing, cheese processing, and sugar clarification. Specific examples include downstream processing of fermentation broths; concentration of protein in milk, whole egg or egg white with simultaneous removal of salts and sugars; and concentration of gelling agents and thickeners like agar, carrageen, pectins, or gelatin. Thus the module is useful for many different fluid separation applications in a variety of fields in the medical, pharmaceutical, industrial, and food industries.

Figure 4:
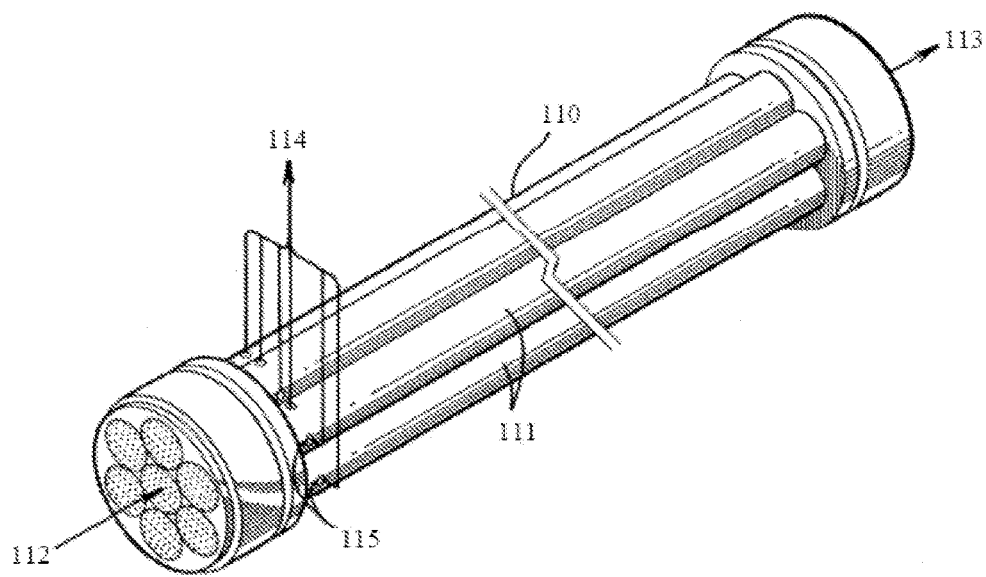
FIG. 4 shows an embodiment of a hollow fiber separation module.

Disclosed in FIG. 4 is an embodiment of a separation module 110 comprising one or more bundles of hollow fibers of the asymmetric membrane. Each fiber bundle may be contained within an enclosure 111 that is substantially impermeable to the fluids to be separated to prevent fluid from passing between adjacent fiber bundles. The hollow fibers may be embedded in and communicate through an encasement 116 at either end of the module. The encasement may comprise a thermoset, such as epoxy, polyester, melamine, polysiloxane, or a polyurethane; or may comprise a thermoplastic, such as polyethylene, polypropylene, poly(ethylene terephthalate), or poly(1,4-butylene terephthalate), for example. The feed stream 112 enters the bore of the fibers at one end of the module and the retentate stream 113 leaves at the opposite end. The encasement may be disposed at ends of the bundles for attaching and sealing to the bundles. The permeate 114 can be recovered from holes 115 disposed in a side of the enclosure, alternatively the permeate may be recovered from holes in the encasement.

Figure 5:
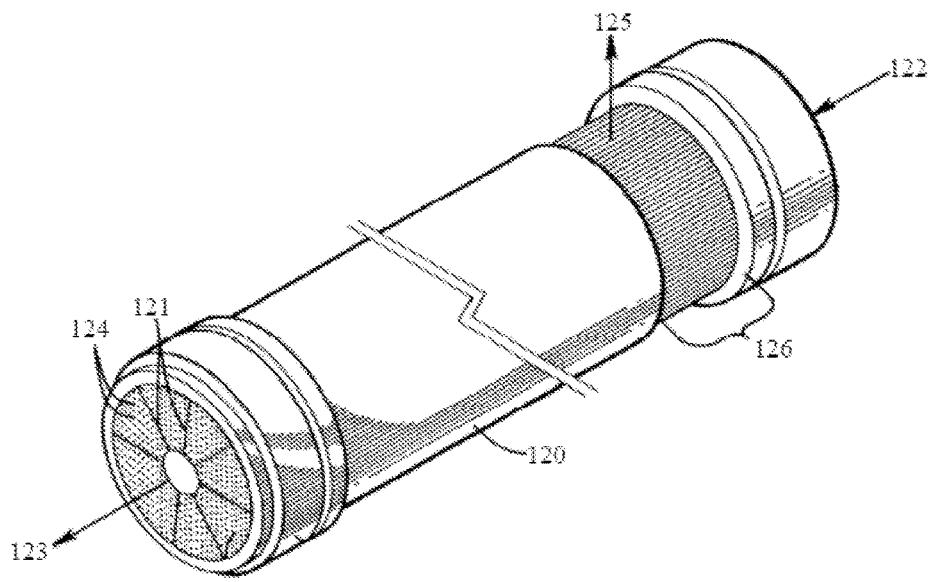
FIG. 5 shows another embodiment of a hollow fiber separation module.

The fiber bundles need not be cylindrical. For example, shown in FIG. 5 is an embodiment of a separation module 120 in which the bundles of fibers are separated by an impermeable barrier 121. In the separation module 120, the feed stream 122 enters the bores of the hollow fibers at one end of the bundles 124 and the retentate stream 123 exits at the opposite end. The permeate fluid 125 can exit the module through an opening 126 in a side of the module.

Figure 6:
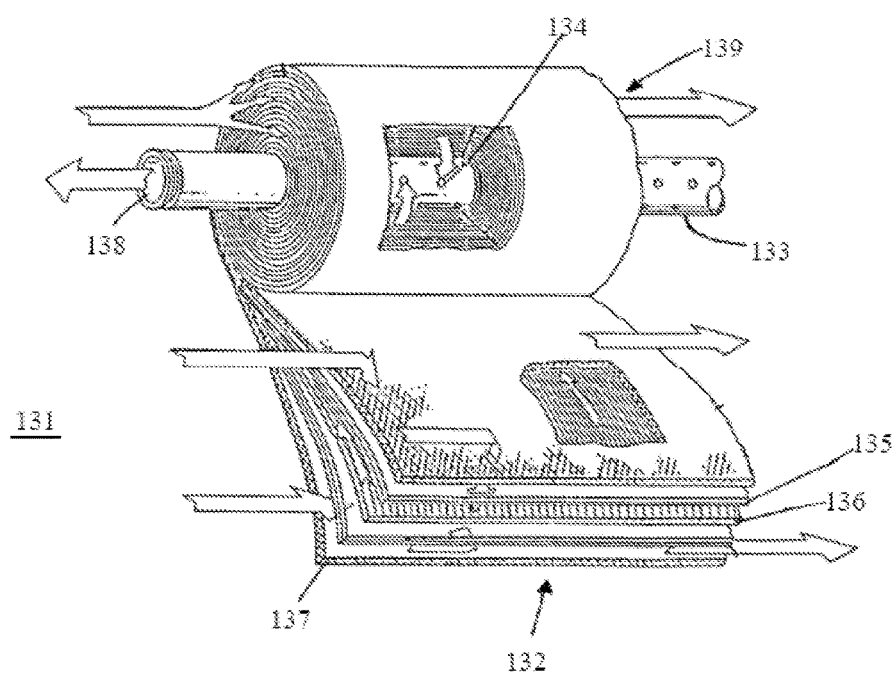
FIG. 6 shows an embodiment of a spiral wound separation module.

The separation module may have a spiral wound design, as shown in FIG. 6. A spiral wound separation module 131 may comprise a sheet of the asymmetric membrane 132 wound onto a hollow core member 133 having perforations 134. Alternatively, the hollow core member 133 may comprise a porous material. Additional layers, such as reinforcing layer 135, inner spacer 136, and outer spacer 137 are also provided. The permeated fluid passes through the perforations 134 in the hollow core member 133 and can be removed through the output 138 of the hollow core member 133. Retentate fluid passes through the outer spacer 137 and exits through the residual output 139.

Figure 7:
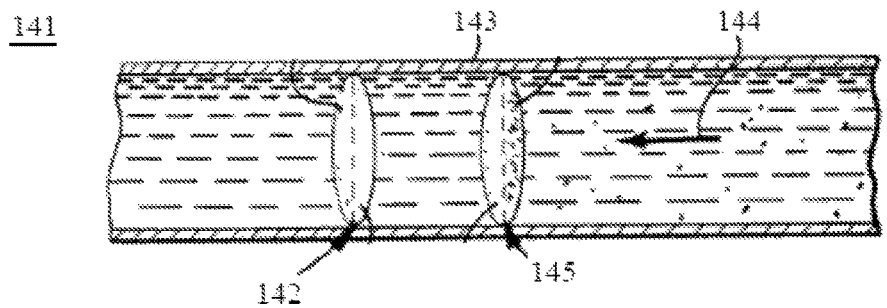
FIG. 7 shows an embodiment of a disk separation module.

The separation module may have a disk design, as shown in FIG. 7. A disk separation module 141 may comprise a filter 142 comprising the asymmetric membrane disposed within a tube 143. The tube may comprise any suitable material, such as a material that is impermeable to the fluid. A support (not shown) may be optionally present. The fluid 144 may contact the disk at a selected pressure sufficient to cause the permeate to pass through the disk. In another embodiment, a plurality of disks may be used, for example to provide a prefilter 145. The prefilter 145 may be the same as or different than the filter 142. For example, the prefilter 145 may have larger pores than the filter 142, or the prefilter 145 may further comprise a functionalized surface, e.g., a surface having a catalyst disposed thereon. In another embodiment the prefilter 145 comprises the asymmetric membrane and the filter 142 comprises a different material.

Figure 8:
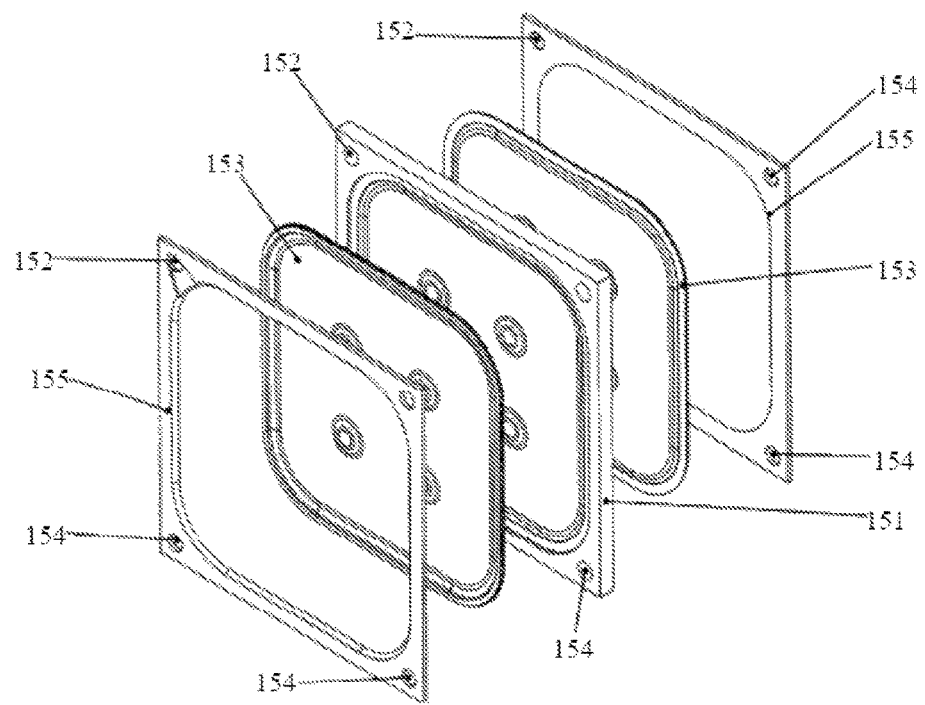
FIG. 8 shows an embodiment of a plate and frame separation module.

The separation module may have a plate and frame design, as shown in the expanded view of FIG. 8. A filter plate of the separation module may comprise a base body 151, the asymmetric membrane 153, and a frame 155, wherein the frame 155 comprises an inlet 152 and an outlet 154. The asymmetric membrane is mounted on one or both sides of the base body and is held in place by a frame mounted in face to face contact with the asymmetric membrane to form the filter plate. The filter can have any suitable shape, and can be square, round, rectangular, or polygonal. The inlet and outlet allow entry of the input stream and exit of the permeate stream. An advantage of the plate and frame design is that the filter media used in making the filter plate assembly can be replaced when desired. The frame 155 and base body may comprise any suitable material, such as a metal, such as steel, or aluminum, or a polymer such as polypropylene or polyethylene. The frame 155 may be fabricated by a molding or a casting process and then machined to the desired size. Due to the solid nature of the frame 155, it can hold the asymmetric membrane 153 to the base body 151 tightly and provide a desirable sealing effect.

Figure 9:
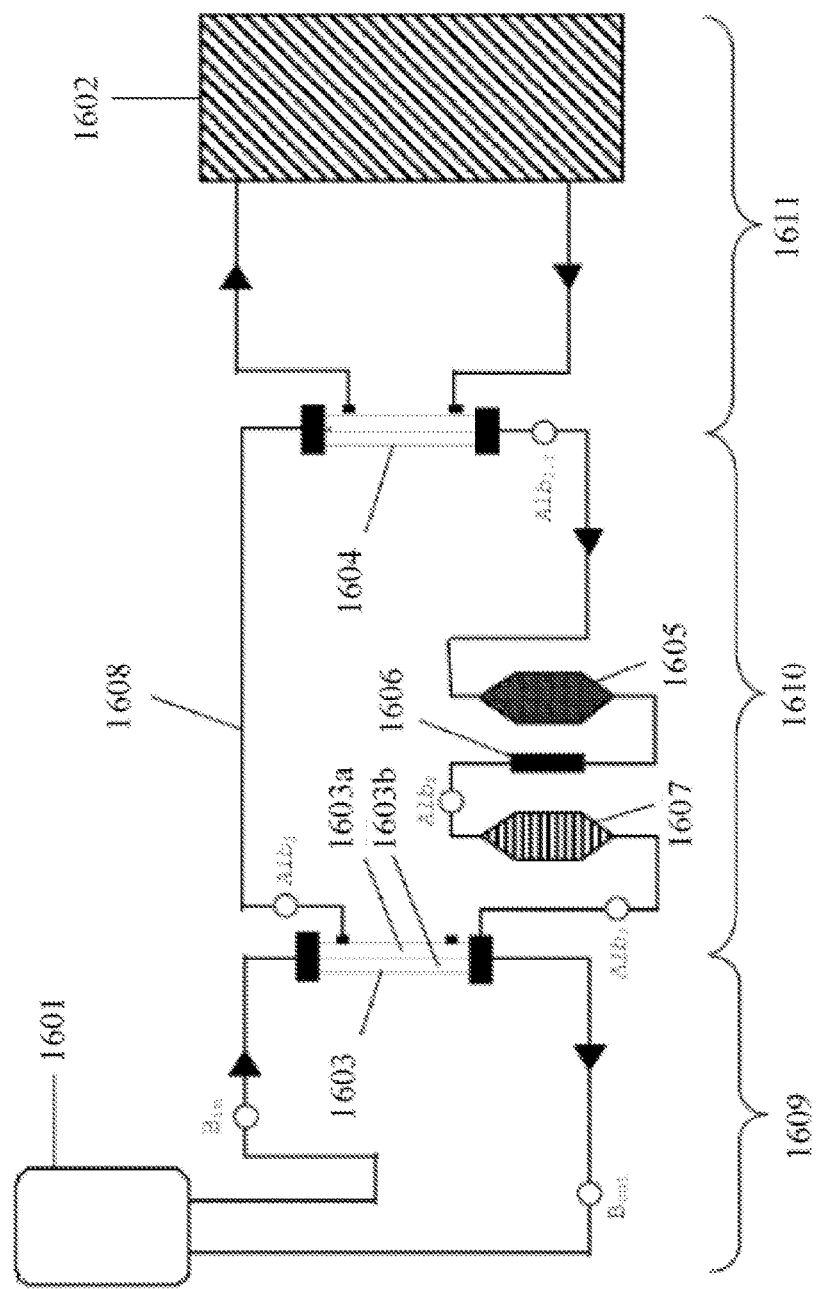
FIG. 9 shows an embodiment of a system for liver dialysis comprising a separation module for liver dialysis.

The porous asymmetric membrane may be particularly suitable for blood dialysis. In liver dialysis systems, blood is cleansed in an extracorporeal circuit that is a combination of both kidney and liver dialysis. In dialysis, blood is circulated through a module containing a dialysis solution to pass the blood across the porous asymmetric membrane. A dialysis solution flows on opposite side of the porous asymmetric membrane, and water and wastes, such as urea uric acid and creatine, move between these two solutions. The cleansed blood is then returned via the circuit back to the body. Disclosed in FIG. 9 is an embodiment of a separation module for liver dialysis and a system for liver dialysis comprising the module. The system comprises a blood circuit 169, an albumin circuit 1610, and a dialysate circuit 1611. As shown in FIG. 9, the patient's 161 blood is passed into a separation module comprising the porous asymmetric membrane. The dialysate side 163a of the separation module 163 provides for clean human albumin that acts as a dialysate. As the patient's blood moves along the membrane, water-soluble and protein bound toxins in the blood are transported through the membrane and into the dialysate albumin solution on the other side 168. The membrane is impermeable to albumin and to other valuable proteins such as hormones and clotting factors, keeping them in the patient's circulation. The cleansed blood then returns to the patient. Meanwhile, the albumin solution carrying the toxins is recycled by passing first through a low-flux dialyzer 164 opposite a buffered aqueous solution 162. This process is similar to that found in kidney dialysis and removes water-soluble substances from the albumin solution. The albumin then passes through an activated carbon adsorber 165 and, after passing a filter which removes carbon particles 166, passes through an anion exchanger 167 that removes toxins bound to albumin. The recycled albumin can then again enter the separation module 163 and bind again to toxins which can thus be removed from the patient's blood.

Similar processes can be used to separate polysaccharides. In a method of separating of polysaccharides, the method may comprise contacting a mixture of sugars, such as dextrose, glucose, and fructose with the asymmetric membrane to separate the polysaccharides and provide a product stream enriched in a selected sugar.

Protein or enzyme recovery is also disclosed. A method for recovering a protein or enzyme of interest from a culture solution using cross-flow membrane filtration is provided, the method comprising: subjecting a culture solution comprising a protein or an enzyme of interest to cross-flow membrane filtration a conditions that cause the protein of interest to be retained in a feed stream to allow purification, concentration, and/or buffer exchange of the protein or enzyme of interest. Alternatively, the membrane allows the passage of the protein or enzyme of interest.

The production of purified water, e.g., drinking water, is also disclosed. Reverse osmosis membranes are designed to remove dissolved salts from water. Water passes readily through the reverse osmosis membrane, whereas dissolved salt is retained. Under natural conditions of osmosis, water will diffuse through a semipermeable membrane toward a region of higher salt concentration in order to equalize solution strength on both sides of the membrane. In order to overcome and reverse this osmotic tendency, pressure is applied to feedwater to force water to permeate from a region of higher salt concentration to lower salt concentration, thereby producing a purified stream.

Figure 10:
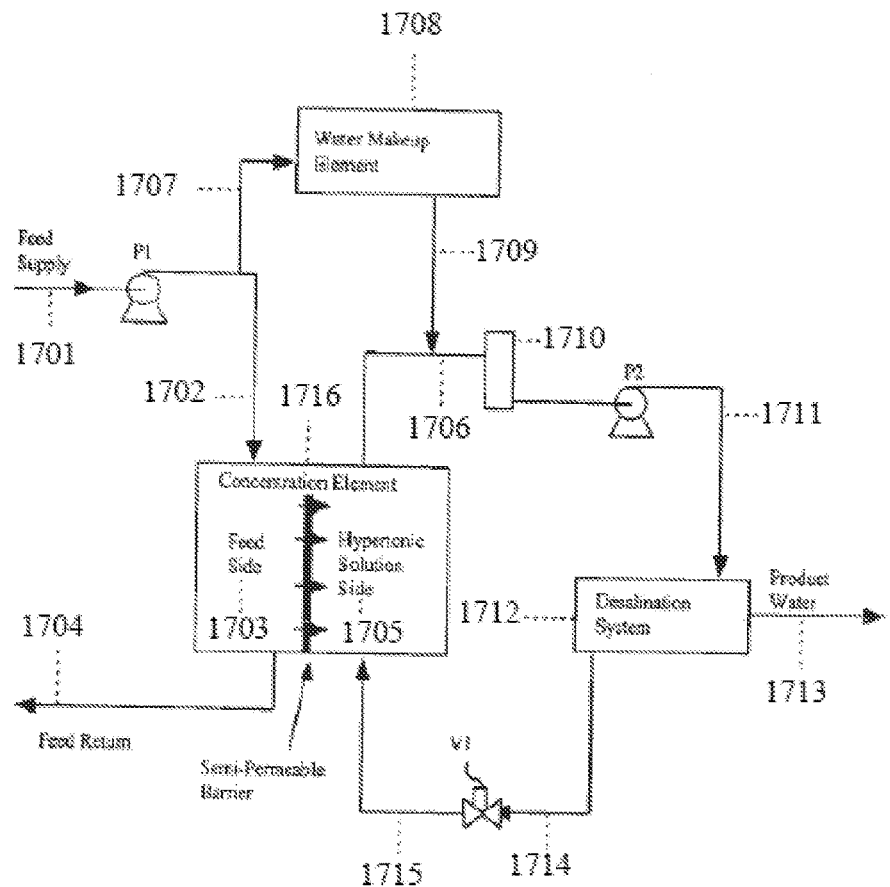
FIG. 10 shows an embodiment of a system for pretreatment of water.

The membrane may have particular application pretreatment of water in a desalination system, an embodiment of which is shown in FIG. 10. The pretreatment may remove or treat any solutes that may that may foul or scale the desalination element. A hypertonic solution can comprise a concentrated feed and its solute composition is the same as that in the feed. However, in a hypertonic solution, contamination components have been concentrated to a level higher than the feed. Additionally, in the hypertonic solution, any solutes that may foul or scale the desalination element can be removed or in some cases addressed by the introduction of anti-scale agents. The membrane separates the feed 173 and the hypertonic solution 175. In such an embodiment, water flows from the feed into the hypertonic solution across the membrane according to water concentration gradients from the feed to the hypertonic solution. Thus, the feed water can be concentrated and the hypertonic solution can be diluted in a concentration module 1716 which comprises the membrane. The hypertonic solution can then be re-concentrated in a desalination system by distillation, electrodialysis or otherwise and then recycled back into a concentration module comprising the membrane. As shown in FIG. 10, feed 171 enters the system through pump P1 and exits by a discharge 174. In the concentration element, the feed 172 can be passed across one side of the separation membrane on the feed side of the concentration module 173. On the permeate side of the membrane is a hypertonic solution. The hypertonic solution can comprise feed water that has been concentrated to a level higher than the feed but lower than its solubility threshold. In the concentration element, water diffuses along concentration gradients from the higher liquid content feed 173 through the membrane and into the lower liquid content hypertonic solution 175. The feed 172 can therefore be concentrated and the hypertonic solution 5 can be diluted in the concentration module 1716. In the desalination system water can be removed from the hypertonic solution. This water becomes the product 1713 of the overall process. The hypertonic solution can be re-concentrated as a result of the removal of the product water. This reconstituted hypertonic solution 1714 can be then passed through valve V1 and returned back to the hypertonic solution side of the concentration module 1715 and the process can be repeated. Lost solute can be made-up by diverting a constant flow of feed 177 back into the hypertonic solution 179. After mixing the feed makeup 179 with the hypertonic solution 176 it can be passed into a permeate holding tank 1710. From tank 1710 the fluid can then be pumped by P2 via 1711 into the desalination system 1712.

Similarly, the module may be used to remove contaminants, including biological contaminants such as bacteria or protozoa, or organic contaminants, such as organic compounds such as polychlorinated biphenyls (PCBs), to produce a purified product stream.

The asymmetric membrane and module are also useful for oxygenation of blood, such in an artificial lung device. An artificial lung device contains a dialyzer module comprising the membrane interposed in the blood circulation of a patient whose normal respiration has been interrupted, for example, while undergoing heart surgery. Blood circulates through the dialyzer module which includes the membrane separating the blood from a suitable oxygen-bearing gas or solution. The membrane is impermeable to liquid but allows carbon dioxide to pass from the blood and oxygen to pass to the blood.

Figure 11:
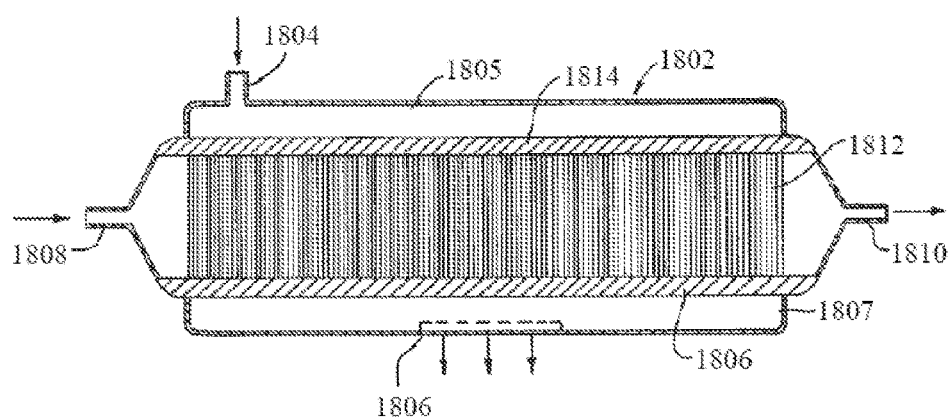
FIG. 11 shows an embodiment of a blood oxygenator.

An embodiment of the blood oxygenator is shown in FIG. 11. A suitable housing 182, in the form shown, has a generally rectangular cross-sectional configuration and is provided with an array of hollow fibers 1812 of the porous asymmetric membrane. In the form shown the fibers are positioned generally vertically and have their ends sealingly secured to a sealing material 1814, 1816. The sealing material may comprise a thermoplastic or a thermoset, such as epoxy, silicone rubber, or polyurethane, for example. The fibers 1812 preferably have a length substantially less than the longitudinal extent of housing. The ends of the fibers 1812 project to the upper and lower extremities respectively of the sealing material 1814, 1816. In this fashion, the gas inlet 184 which is in communication with inlet chamber 185 is in communication with the open ends of the fibers 1812 thereby permitting oxygen to be introduced through the gas inlet 184 and into the fibers 1812 for flow downwardly therethrough. Similarly, the lower ends of the fibers 1812 are in communication with the gas outlet 186 through outlet chamber 187. Blood entering the oxygenator through blood inlet 188 will flow generally from one end of the oxygenator to the other and emerge through blood outlet 1810. In flowing through the oxygenator, it will be noted that the blood flows in a direction which is generally transverse to and preferably substantially perpendicular to the axial orientation of the fibers.

Figure 12:
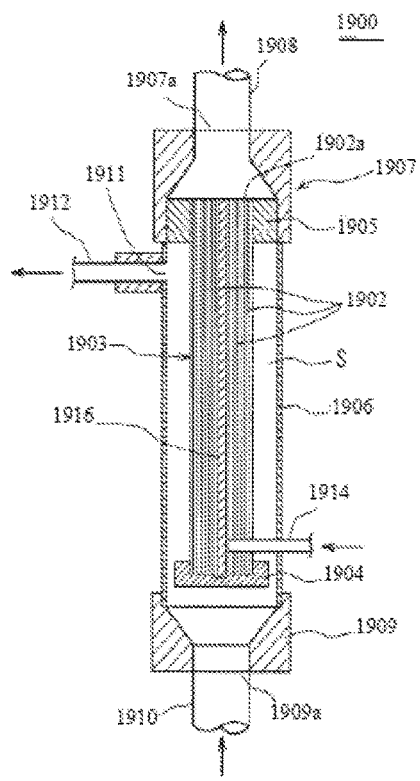
FIG. 12 shows an embodiment of a separation module for wastewater treatment.
Figure 13:
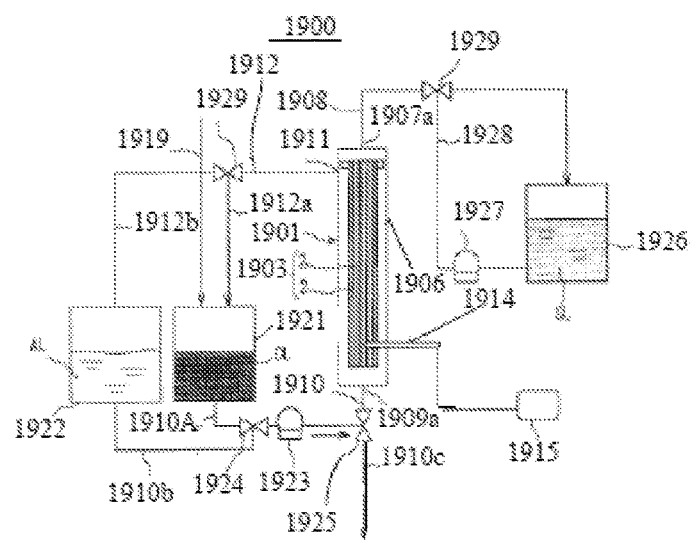
FIG. 13 shows an embodiment of a system for wastewater treatment.

The porous asymmetric membrane is also useful for wastewater treatment. An embodiment of a separation module for treatment of oil-containing wastewater is shown in FIG. 12, and a system for wastewater treatment comprising the separation module for oil-containing wastewater treatment is shown in FIG. 13. The separation membrane module 191 includes an assembly 193 in which a plurality of hollow fiber membranes 192 are gathered together, the lower end of the assembly 193 is sealed with a sealing member 194, and a lower open end of each hollow fiber membrane 192 is closed. The upper end of the assembly 193 is fixed with a fixing member 195 with an upper open end 192a of each hollow fiber membrane 192 being in an open state. The assembly 193 is housed in an external cylinder 196. An upper cap 197 is attached by bonding to the upper end of the external cylinder 196. An outlet port 197a is provided such that the inside of the upper cap 197 communicates with the hollow portion of each hollow fiber membrane 192, and the outlet port 197a is connected to an outlet pipe 198 for taking out treated liquid. A lower cap 199 is fixed by bonding to the lower end of the external cylinder 196. An inlet port 199a for liquid to be treated, i.e., oil-containing wastewater, is provided on the lower cap 199, and the inlet port 199a is connected to an inlet pipe 1910 which introduces the liquid to be treated. A space S is secured between the sealing member 4 at the lower end of the assembly 193 and the inner wall of the external cylinder 196 so that oil-containing wastewater introduced from the inlet port 199 a can promptly flow into the assembly 3 inside the external cylinder 196. Furthermore, a discharge port 1911 for non-filtered, untreated liquid is provided at the peripheral wall in the vicinity of the upper end of the external cylinder 196, and the discharge port 1911 communicates with a circulation pipe 1912. Furthermore, the upper fixing member 195 and the lower sealing member 194 are joined by a reinforcing bar 1916 at the center. The reinforcing bar 1916 prevents the non-rigid hollow fiber membranes 192 from being lifted by the force of stream of oil-containing wastewater from the lower part and is provided to secure verticality. Regarding the system for wastewater treatment as shown in FIG. 13, system 1920 includes an oil-containing wastewater storage tank 1921 into which oil-containing wastewater OL is continuously poured from a pipe 1919, a cleaning liquid storage tank 1922 which stores a cleaning liquid composed of an alkaline aqueous solution (hereinafter referred to as an "alkaline cleaning liquid") AL, the inlet pipe 1910 through which each of the oil-containing wastewater storage tank 1921 and the cleaning liquid storage tank 1922 communicates with an inlet portion 199*a* for liquid to be treated of the separation membrane module 191 and which is inserted with a pump 1923 and a switching valve 1924, and the circulation pipe 1912 through which each of the oil-containing wastewater storage tank 1921 and the cleaning liquid storage tank 1922 communicates with the discharge port 1911 for non-filtered, untreated liquid of the separation membrane module 1. The inlet pipe 1910 is provided with the switching valve 1924 on the upstream side of the pump 1923, and the pipe is branched by the switching valve 1924. A branch pipe 1910A is connected to the oil-containing wastewater storage tank 1921, and a branch pipe 1910B is connected to the cleaning liquid storage tank 1922. Furthermore, the inlet pipe 1910 is connected to a discharge pipe 1910C for backwash water through a switching valve 1925 on the downstream side of the pump 1923. The circulation pipe 1912 serving as a cleaning liquid path is also branched. A branch pipe 1912A is connected to the oil-containing wastewater storage tank 1921, and a branch pipe 1912B is connected to the cleaning liquid storage tank 1922. Furthermore, by inserting a switching valve 1929 at the branching position, a non-filtered, untreated liquid is returned to the oil-containing wastewater storage tank 1921, and the alkaline cleaning liquid is returned to the cleaning liquid storage tank 1922 for circulation during alkali cleaning.

The outlet pipe 198 which is connected to the outlet port 197*a* for filtered, treated liquid SL and takes out treated liquid is connected to a treated liquid storage tank 1926. At the same time, since the treated liquid stored in the treated liquid storage tank 1926 is used as backwash water, a backwash pipe 1928 inserted with a backwash pump 1927 is connected between the treated liquid storage tank 1926 and the outlet pipe 198. A diffusion air inlet pipe 1914 is connected to a blower 1915 inserted into the pipe 1910 close to the inlet port 1936*a* of the separation membrane module 1931, and thereby, diffusion air is fed into the hollow fiber membranes 1932.

Figure 14:
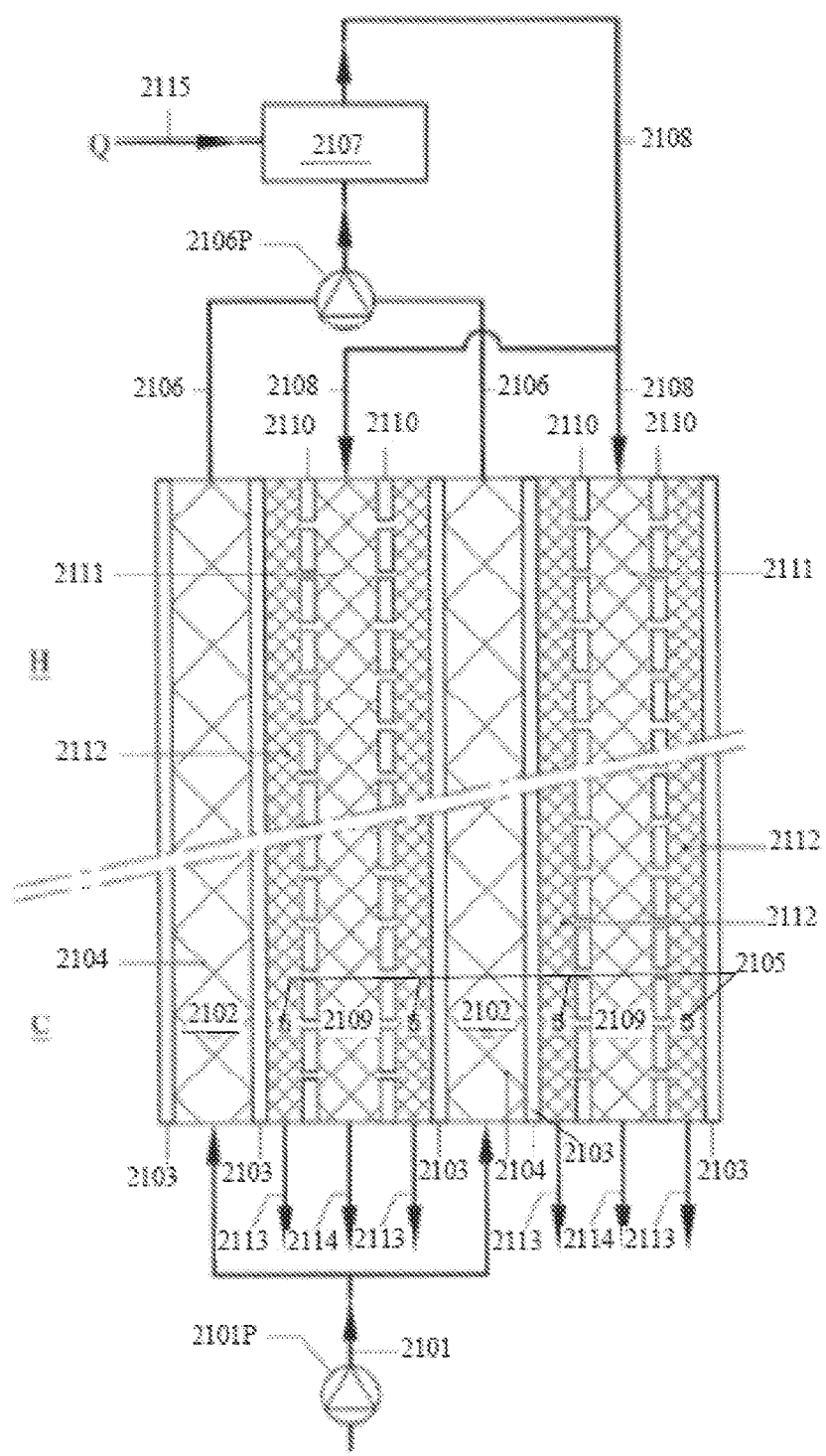
FIG. 14 shows an embodiment of a module for membrane distillation.

The asymmetric membrane is also suitable for membrane distillation. The method of membrane distillation includes passing a heated vaporizing stream of a liquid through a porous membrane, whereby a vapor of the liquid flows via the pores of the membrane to the other side of the membrane, and condensing the vapor on the other side of the membrane to give a distillate stream. An embodiment of a module for membrane distillation is shown in FIG. 14. As shown in FIG. 14, the module is divided into a cold side C and a hot side H. A relatively cold feed stream 211 is pumped with feed pump 1P into the parallel feed channels 212, at the cold side C. These feed channels are constructed by the non-porous walls 213 and a spacer material 214. In these feed channels 212, the feed stream is heated by taking up heat from the warmer distillate channels 215 at the other side of the walls 213. So, gradually the feed stream becomes hotter and leaves the module as stream 216 at the hot side H, with the aid of pump 6P. This pump ensures by suction that the pressure in the feed channels 212 is relatively low; typically between 0.1 and 3.0 bar (absolute pressure). The relatively hot feed stream 216 is pumped into a heat exchanging device 217, where it is heated further by an external heat input 2115, (the heat used can be waste heat, solar heat, steam, hot solid material, etc.), and leaves the device as relatively hot retentate stream 218. Stream 218 enters the module at the hot side H, and flows through the parallel placed retentate channels 219 in more or less counter-current flow with stream 211. The retentate channels 219 are constructed by the porous asymmetric membranes 2110 and the spacer material 2111. In these retentate channels, the retentate stream 218 gradually becomes cooler because of evaporation of water vapor, and some heat conduction, through the porous asymmetric membranes 2111 into the distillate channels 215, where the water vapor condenses forming a pure, liquid distillate 2113. The distillate channels are delimited by the porous asymmetric membrane 2110 at one side and a non-porous condenser wall 213 at the other side. Inside channels 215, a spacer material 2112 can be optionally disposed. The released heat in the distillate channels 215 is primarily transferred through walls 213 into the feed stream 211, flowing in the feed channels 212. The liquid distillate leaves the module preferably at the cold side C, by which also heat of stream 2113 is recovered and transferred into stream 211. It can, however, also be discharged at both sides C and H of the module. This discharge can take place by gravity, pumping, and/or by pressure build up inside channels 215 as a result of the water produced. The relatively cool and concentrated retentate stream leaves the module at the cold side C as stream 2114. For a large part of the module, especially the hot side H, the absolute liquid pressure inside the retentate channels 219 is higher than in the corresponding feed channels 212. The absolute liquid pressures in the retentate channels can range between 1.0 and 4.0 bar, for example.

In addition, the module is useful for separating gases and/or vapors from mixtures of liquids or mixtures of liquids gases using the membrane separation processes of membrane stripping, membrane distillation. In membrane stripping, a material permeating through or across the membrane is removed from the module as a gas or a vapor. In membrane distillation, a membrane is used and the material permeating through or across the membrane is condensed and removed from the device as a liquid.

The invention includes at least the following embodiments.

Embodiment 1

A porous asymmetric membrane comprising, consisting essentially of, or consisting of: a hydrophobic polymer comprising, consisting essentially of, or consisting of a poly(phenylene ether) or poly(phenylene ether) copolymer; and an amphiphilic block copolymer comprising a hydrophobic block comprising a polystyrene block; and a hydrophilic block or graft.

Embodiment 2

A porous asymmetric membrane-forming composition comprising, consisting essentially of, or consisting of: a hydrophobic polymer comprising, consisting essentially of, or consisting of a poly(phenylene ether) or poly(phenylene ether) copolymer; an amphiphilic block copolymer comprising a hydrophobic block comprising a polystyrene block, and a hydrophilic block or graft; and a water-miscible polar aprotic solvent; wherein the hydrophobic polymer and amphiphilic block copolymer are dissolved in the water-miscible polar aprotic solvent.

Embodiment 3

A method of forming a porous asymmetric membrane, the method comprising: dissolving a hydrophobic polymer comprising, consisting essentially of, or consisting of a poly(phenylene ether) or poly(phenylene ether) copolymer and an amphiphilic block copolymer comprising a hydrophobic block comprising a polystyrene block, and a hydrophilic block or graft, in a water-miscible polar aprotic solvent to form a porous asymmetric membrane-forming composition; phase-inverting the porous asymmetric membrane forming-composition in a first non-solvent to form the porous asymmetric membrane; optionally washing the porous asymmetric membrane in a second non-solvent; and optionally drying the porous asymmetric membrane to form the porous asymmetric membrane.

Embodiment 4

The porous asymmetric membrane, composition, or method of any one or more of embodiments 1-3, wherein the hydrophobic polymer comprises a poly(phenylene ether) having repeat units independently having the structure (I), wherein each occurrence of $Z^1$ is independently halogen, unsubstituted or substituted $C_{1-12}$ hydrocarbyl provided that the hydrocarbyl group is not tertiary hydrocarbyl, $C_{1-12}$ hydrocarbylthio, $C_{1-12}$ hydrocarbyloxy, or $C_{2-12}$ halohydrocarbyloxy wherein at least two carbon atoms separate the halogen and oxygen atoms; and each occurrence of $Z^2$ is independently hydrogen, halogen, unsubstituted or substituted $C_{1-12}$ hydrocarbyl provided that the hydrocarbyl group is not tertiary hydrocarbyl, $C_{1-12}$ hydrocarbylthio, $C_{1-12}$ hydrocarbyloxy, or $C_{2-12}$ halohydrocarbyloxy wherein at least two carbon atoms separate the halogen and oxygen atoms.

Embodiment 5

The porous asymmetric membrane, composition, or method of any of embodiments 1-3, wherein the hydrophobic polymer comprises a poly(phenylene ether) copolymer comprising: 100 to 20 mole percent repeat units derived from 2,6-dimethylphenol; and 0 to 80 mole percent repeat units derived from a second monohydric phenol (II) wherein Z is $C_{1-12}$ alkyl, $C_{3-12}$ cycloalkyl, or monovalent group (III)

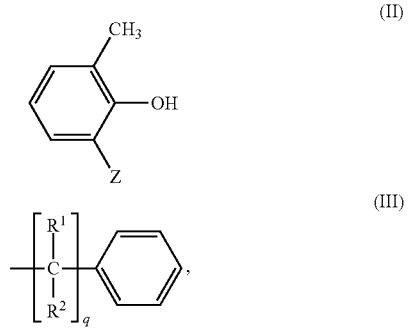

wherein q is 0 or 1, and $R^1$ and $R^2$ are independently hydrogen or $C_1$-$C_6$ alkyl; wherein the mole percents are based on the total moles of all repeat units; and wherein the poly(phenylene ether) copolymer has an intrinsic viscosity of 0.7 to 1.5 deciliters per gram, measured in chloroform at 25° C.

Embodiment 6

The porous asymmetric membrane, composition, or method of embodiment 5, wherein the hydrophobic polymer comprises a poly(phenylene ether) copolymer comprising: 80 to 20 mole percent repeat units derived from 2,6-dimethylphenol; and 20 to 80 mole percent repeat units derived from the second monohydric phenol.

Embodiment 7

The porous asymmetric membrane, composition, or method of embodiment 6, wherein the second monohydric phenol comprises 2-methyl-6-phenylphenol.

Embodiment 8

The porous asymmetric membrane, composition, or method of any of embodiments 1-7, wherein the hydrophobic polymer has an intrinsic viscosity of 0.7 to 1.5 deciliters per gram, measured in chloroform at 25° C.

Embodiment 9

The porous asymmetric membrane, composition, or method of any of embodiments 1-8, wherein the solubility of the hydrophobic polymer in the water-miscible polar aprotic solvent is 50 to 400 grams per kilogram at 25° C., based on the combined weight of the poly(phenylene ether) copolymer and the solvent.

Embodiment 10

The porous asymmetric membrane, composition, or method of any of embodiments 1-9, wherein the amphiphilic block copolymer comprises 20 to 50 weight percent of the hydrophobic block and 50 to 80 weight percent of the hydrophilic block or graft.

Embodiment 11

The porous asymmetric membrane, composition, or method of any of embodiments 1-10, wherein the hydrophilic block or graft of the amphiphilic block copolymer comprises a polymerized hydrophilic ethylenically unsaturated monomer.

Embodiment 12

The porous asymmetric membrane, composition, or method of embodiment 11, wherein the hydrophilic ethylenically unsaturated monomer comprises methoxy-capped poly(ethylene oxide) methacrylate, 4-vinylpyridine, N-vinylpyrrolidone, N,N-dimethylacrylamide, 4-acryloylmorpholine, or a combination comprising at least one of the foregoing.

Embodiment 13

The porous asymmetric membrane, composition, or method of any one or more of claims 1 to 10, wherein the hydrophilic block comprises poly(ethylene oxide) or a copolymer of ethylene oxide with 1,2-propylene oxide, 1,2-butylene oxide, styrene oxide, or a combination comprising at least one of the foregoing.

Embodiment 14

The porous asymmetric membrane, composition, or method of any one or more of embodiments 1-10, wherein the hydrophilic block of the amphiphilic block copolymer comprises poly(ethylene oxide).

Embodiment 15

The porous asymmetric membrane, composition, or method of any of embodiments 1-14, wherein a hydrophilic polymer is excluded.

Embodiment 16

The porous asymmetric membrane, composition, or method of embodiment 15, wherein the hydrophilic polymer comprises poly(N-vinylpyrrolidone), a poly(oxazoline), poly(ethylene oxide), poly(propylene oxide), a poly(ethylene oxide) monoether or monoester, a poly(propylene oxide) monoether or monoester, a block copolymer of poly(ethylene oxide) and poly(propylene oxide), polysorbate, cellulose acetate, glycosaminoglycans such as heparin or heparin sulfate, or a combination comprising at least one of the foregoing.

Embodiment 17

The porous asymmetric membrane, composition, or method of any of embodiments 1-16, further comprising poly(2,6-dimethyl-1,4-phenylene ether), polyethersulfone, polysulfone, polyphenylsulfone, or a combination comprising at least one of the foregoing.

Embodiment 18

The porous asymmetric membrane of any of embodiments 1 or 4-17, wherein a configuration of the porous asymmetric membrane is a sheet, disc, spiral wound, plate and frame, hollow fiber, capillary, and tubular.

Embodiment 19

The porous asymmetric membrane of any of embodiments 1 or 4-17, wherein the membrane is a porous asymmetric flat sheet.

Embodiment 20

The porous asymmetric membrane of embodiments 1 or 4-17, wherein the asymmetric membrane is in a form of a spiral.

Embodiment 21

The porous asymmetric membrane of any one of embodiments 1 or 4-17, wherein the membrane is a porous asymmetric hollow fiber.

Embodiment 22

A separation module comprising the porous asymmetric membrane of any of embodiments 1, 4-17, or 18-21.

Embodiment 23

The separation module of embodiment 22, wherein the separation module is designed for dead-end filtration, outside-in filtration, inside-out filtration, or cross-flow filtration.

Embodiment 24

The separation module of embodiment 22, wherein the separation module is selected from a microfiltration module, a nanofiltration module, an ultrafiltration module, a reverse osmosis module, a water pretreatment module, or a membrane distillation module.

Embodiment 25

The separation module of any of embodiments 22-24, comprising a bundle of asymmetric hollow fibers.

Embodiment 26

The separation module of embodiment 25, wherein the bundle of asymmetric hollow fibers are disposed within an enclosure configured for fluid separation.

Embodiment 27

The separation module of embodiments 25 or 26, wherein the separation module comprises: an enclosure configured to contain the bundle, the enclosure having an outlet configured for withdrawing a permeate fluid; a first encasement comprising a thermoset or a thermoplastic polymeric material and located at a first end of the bundle, arranged such that the hollow fiber membranes are embedded in the first encasement and communicate through the first encasement and are open on an outer face of the first encasement; a second encasement comprising a thermoset or a thermoplastic polymeric material and located at a second end of the bundle opposite the first end of the bundle, arranged such that the hollow fiber membranes are embedded in the second encasement and communicate through the second encasement and are open on an outer face of the second encasement; a first end cap arranged and configured for attaching and sealing to the first end of the bundle or enclosures at or near the first encasement; a second end cap arranged and configured for attaching and sealing to the second end of the bundle or enclosures at or near the second encasement; an inlet for introducing a fluid mixture to be separated into bores of the hollow fiber membranes at the first encasement; and an outlet for withdrawing a retentate fluid from the bores for the hollow fiber membranes at the second encasement.

Embodiment 28

The separation module of any of embodiments 25-27, comprising a plurality of bundles.

Embodiment 29

The separation module of any of embodiments 22-24, wherein separation module comprises: a hollow core comprising perforations; the asymmetric membrane wound around the core; and a spacer disposed adjacent the asymmetric membrane.

Embodiment 30

A separation module that is a spiral wound module comprising the porous asymmetric flat sheet of embodiment 19.

Embodiment 31

A separation module that is a hollow fiber module comprising 10 to 10,000 of the porous asymmetric hollow fibers of embodiment 21.

Embodiment 32

A method of filtration comprising passing a feedstream through the separation module of any of embodiments 22-31 such that it contacts a first side of the porous asymmetric membrane, and passing a permeate through the porous asymmetric membrane to provide a permeate stream and a concentrated feedstream.

Embodiment 33

A dialysis device for conducting hemodialysis on a patient suffering from liver failure, the device comprising the porous asymmetric membrane of claim 1, 4-17, or 18-21.

Embodiment 34

The dialysis device of embodiment 33, wherein the dialysis device comprises the separation module of any of embodiments 22-31.

Embodiment 35

The dialysis device of embodiment 34, wherein the asymmetric membrane allows the passage of molecules having a molecular weight of up to 45 kilodaltons with a sieving coefficient of 0.1 to 1.0 in the presence of whole blood, wherein the dialysis device reduces the concentration of protein-bound toxins and inflammatory cytokines in the blood of the patient, wherein the dialysis device reduces the concentration of unconjugated bilirubin and bile acids in the blood of the patient, wherein the dialysate passing the said dialysis membrane comprises from 1% to 25% human serum albumin.

Embodiment 36

A method of dialysis, the method comprising passing blood through the separation module of embodiment 34 or 35 such that it contacts a first side of the porous asymmetric membrane, and passing a dialysis solution through the separation module such that it contacts a second opposite side of the porous asymmetric membrane to remove waste products from the blood.

Embodiment 37

A method for the treatment of liver failure, the method comprising conducting hemodialysis on a patient suffering from liver failure using a liver dialysis device comprising the porous asymmetric membrane of any of embodiments 1, 4-17, or 18-21.

Embodiment 38

The method for the treatment of liver failure of embodiment 37, wherein the dialysis device comprises the separation module of embodiments 22-31.

Embodiment 39

A method of sugar purification, the method comprising passing a fluid comprising a combination of polysaccharides through the separation module of any of embodiments 22-31 such that the fluid contacts a first side of the porous asymmetric membrane, and passing a polysaccharide through the membrane to purify the sugar.

Embodiment 40

A method of protein or enzyme recovery comprising: urging a fluid comprising a protein or enzyme through the separation module of any of embodiments 22-31 such that the fluid contacts a first side of the porous asymmetric membrane; and removing a component from the fluid by passing the component through the membrane to provide a retentate stream enriched in the protein or enzyme to recover the protein or enzyme.

Embodiment 41

A method of water purification comprising: passing a feedwater through the separation module of any of embodiments 22-31 such that the feedwater contacts a first side of the porous asymmetric membrane with a pressure greater than osmotic pressure to produce purified water.

Embodiment 42

A water pretreatment system comprising: a concentration module comprising the porous asymmetric membrane of any of embodiments 1, 4-17, or 18-21 for concentrating a feed and diluting a recirculating hypertonic solution to produce a slipstream; and a water makeup element for receiving the slipstream and combining the slipstream with the hypertonic solution to provide solutes to the recirculating hypertonic solution, wherein the recirculating hypertonic solution is suitable for desalination.

Embodiment 43

The water pretreatment system of embodiment 42, wherein the concentrator comprises the separation module of any of embodiments 22-31.

Embodiment 44

A method of pretreating water, the method comprising: receiving a feedwater; separating the feed water into a concentrator feed and a slipstream; processing the concentrator feed in a concentrator comprising the porous asymmetric membrane of any of embodiments 1, 4-17, or 18-21 to generate a hypertonic solution; combining the slipstream and the hypertonic solution to generate an effluent capable of decomposition into purified water and a recirculating hypertonic solution.

Embodiment 45

The method of embodiment 44, wherein the concentrator comprises the separation module of any of embodiments 22-31.

Embodiment 46

A blood oxygenator comprising: a housing, a plurality of hollow fibers comprising the porous asymmetric membrane of any of embodiments 1, 4-17, or 18-21 disposed within the housing for transporting a first fluid therethrough, a first inlet in fluid communication with the fibers for delivering the first fluid thereto, a first outlet in fluid communication with the fibers for receiving the first fluid therefrom, a second inlet and a second outlet in communication with regions disposed exteriorly of the hollow fibers.

Embodiment 47

The blood oxygenator of embodiment 46, wherein the porous asymmetric membrane is contained within the separation module of any of embodiments 22-31.

Embodiment 48

The blood oxygenator of embodiment 47, wherein the first fluid is blood, and wherein the second fluid is an oxygen containing gas.

Embodiment 49

The blood oxygenator of embodiment 47, wherein the first fluid is blood, and wherein the second fluid is a liquid which comprises molecular oxygen.

Embodiment 50

A separation module for oil-containing wastewater treatment, which separates water-insoluble oil from oil-containing wastewater, the separation module comprising the porous asymmetric membrane of any of embodiments 1, 4-17, or 18-21.

Embodiment 51

A system for wastewater treatment comprising the separation module of embodiment 50.

Embodiment 52

A method of wastewater treatment comprising treating an oil-containing wastewater with the system of embodiment 51.

Embodiment 53

The method of embodiment 52 further comprising directing a cleaning liquid comprising an alkaline aqueous solution to a surface of the porous asymmetric membrane to remove water-insoluble oil adhering to the surface of the porous asymmetric membrane of the separation module.

Embodiment 54

An ultrafiltration device, the device comprising: a filter housing for a separation module, the filter housing comprising an inlet and an outlet, and a bundle of tubular or capillary ultrafiltration membranes of any one or more of claims of any of embodiments 1, 4-17, or 18-21 fitted in the filter housing, the tubular or capillary membranes being permanently hydrophilic, whereby the tubular or capillary membranes are open at a first inlet end and sealed at the other end and are, at the first end, held in a membrane holder which closes off the space in between the capillary membranes and the filter housing wherein the pore size of the tubular or capillary ultrafiltration membranes decreases in the direction of the liquid flow.

Embodiment 55

An apparatus for purification of a liquid by membrane distillation comprising a feed channel; a distillate channel; and a retentate channel, wherein the distillate channel and the retentate are separated by the porous asymmetric membrane of any of embodiments 1, 4-17, or 18-21.

Embodiment 56

The apparatus for purification of a liquid by membrane distillation of embodiment 55, whereby the apparatus comprises a segment comprising a first distribution chamber for a feed liquid to be supplied, a second distribution chamber located opposite the first distribution chamber for feed liquid to be discharged, a third distribution chamber for retentate stream to be supplied and a fourth distribution chamber opposite the third the third distribution chamber for the retentate stream to be discharged, whereby the segment is provided with a first pump for pumping the feed stream pressure into the segment and a second pump which is arranged downstream the second distribution chamber for pumping the retentate stream under pressure into the retentate channel, the wall between the feed channel and the distillate channel comprises a condenser surface in the form of a non-porous membrane, and the wall between the retentate channel and the distillate channel comprises the porous asymmetric membrane, and wherein inside the retentate channel a further channel is arranged for allowing a fluid stream to be brought into heat transfer contact with the retentate stream.

The invention is further illustrated by the following non-limiting examples.

PREPARATIVE EXAMPLES: SYNTHESIS OF MPP-DMP COPOLYMERS

The preparation, characterization and properties of poly(phenylene ether)s has been described by G. Cooper and J. Bennett in *Polymerization Kinetics and Technology*, Vol. 128, pp. 230-257, Jun. 1, 1973 (ACS *Adv. in Chem. Series*). MPP-DMP copolymers were prepared by dissolving the monomers in toluene and conducting oxidative copolymerization with copper-diamine catalyst complexes in the presence of oxygen. The copolymerizations were conducted in a bubbling polymerization reactor equipped with a stirrer, temperature control system, nitrogen padding, oxygen bubbling tube, and computerized control system. The reactor was also equipped with a feeding pot and pump for dosing reactants into the reactor. When the desired degree of polymerization was achieved, the flow of oxygen was stopped and the copper was removed by liquid-liquid extraction with a water-soluble chelating agent. The DMP-MPP copolymers were recovered via non-solvent precipitation by pouring the toluene solution into an excess of methanol with vigorous stirring followed by drying in an oven at 120° C. under a stream of dry nitrogen. Glass transition temperatures (Tg) were determined using differential scanning calorimetry (DSC). The molecular weight distributions of the polymers were characterized via size-exclusion chromatography methods employing chloroform as the mobile phase and calibration against a polystyrene standard. Alternatively the degree of polymerization was characterized by measurement of intrinsic viscosity (IV) in $CHCl_3$ using the Ubbelohde method.

TABLE 3

Characterization of MPP-DMP Copolymers
of Preparative Examples 1-4 and 11-13

| Ex. No. | MPP/DMP (mole/mole) | GPC Mn (g/mole) | GPC Mw (g/mole) | GPC D (Mw/Mn) | IV in CHCl$_3$ (dL/g) | Tg ° C. |
|---|---|---|---|---|---|---|
| 1 | 50/50 | 20,213 | 219,130 | 10.8 | 0.83 | 185 |
| 2 | 20/80 | 50,310 | 172,100 | 3.4 | 1.04 | 210 |
| 3 | 50/50 | 39,820 | 194,900 | 4.9 | 0.97 | 187 |
| 4 | 80/20 | 22,620 | 241,000 | 10.7 | 0.96 | 177 |
| 11 | 20/80 | 63,010 | 210,800 | 3.3 | 1.14 | — |
| 12 | 50/50 | 42,460 | 216,200 | 5.1 | 0.98 | — |
| 13 | 80/20 | 36,490 | 310,700 | 8.5 | 1.08 | — |

Examples 5-10: General Procedure for Casting Membranes Via Solvent/Non-Solvent Phase Inversion Process The polymer was dissolved in chromatography grade NMP totaling 8-10 g in a 20-mL glass vial, sealed tightly, and placed on a low speed roller for 13-48 hr. until a homogenous solution was formed. The solution was poured in an oblong puddle and an adjustable height doctor blade was used to drag across the glass plate at a constant speed by hand. The entire glass plate bearing the cast polymer film was fully submerged into an initial non-solvent bath (25-100 wt. % DI water in NMP) until the membrane begins to lift off the plate. The membrane was transferred off of the glass plate into the intermediate non-solvent bath of 100 wt. % DI water and weighed down at the corners with glass stoppers to allow the exchange of NMP into the water. After 15-45 min. the membrane was transferred to a final non-solvent bath of 100 wt. % water overnight to fully solvent exchange the NMP. The membrane was dried at room temperature. Characterization was performed on pieces cut from the center and most uniform portion of the membrane. The viscosity of the copolymer solutions in NMP was measured at 20° C. using a Brookfield RDV-III Pro viscometer equipped with a small-sample adapter and cylindrical spindle.

Characterization of Membranes

The surface porosities and cross-sectional morphologies of the membranes were characterized using Carl Zeiss Supra VP scanning electron microscopy (SEM). The "top" membrane surfaces (those that were first in contact with the NMP/water bath) were imaged for selective surface morphology. The membrane samples were coated with ~0.3 nm Pt/Pd target using Cressington 208 high resolution sputter coater equipped with thickness controller MTM-20. The surface morphology was imaged using low voltage capability (≤5 kV, probe current 200 nA and inlens surface sensitive detection mode at 100,000× magnifications. A minimum of 3 images were combined for digital image analysis using Clemex Vision PE 6.0.035 software to estimate the pore size distributions and pooled for the analysis. Samples for cross-sectional imaging were soaked in ethanol for 5 min. and cryo-fractured using liquid nitrogen, then allowed to come to room temperature and dried in air. The cryo-fractured membrane samples were coated with Pt/Pd target and imaged using SEM for cross sectional morphology.

The interaction of the membrane surfaces with water was quantified via measurement of contact angle using a Kruss DA-25 drop shape analysis system. A small square section of membrane was cut from the center of the membrane, and mounted on a glass microscope slide using double-sided tape. A 2-μL water droplet was deposited on the surface. Drop shape was measured using digital curve fitting 5 times with a 1 sec. spacing. Resulting contact angles of the water droplet with the membrane surface were averaged.

Examples 9-10: Membranes Cast from 20/80 MPP-DMP Copolymer with PS-PEO Diblock Copolymer A sample of an amphiphilic block diblock copolymer was obtained from Sigma-Aldrich, which is described in their catalog as being comprised of a block of polystyrene (PS) having an Mn of about 30,000 g/mole, which has been coupled to a block of poly(ethylene oxide) (POE) of Mn of about 1,000 g/mole. From this description we conclude that this PS/PEO block copolymer contains only about 3 wt. % of hydrophilic block by weight. In Examples 9 and 10, solutions containing 16 wt. % of the 20/80 MPP-DMP copolymer of Example 2 were prepared in the presence of 2 and 4 wt. % of the PS/PEO diblock copolymer, respectively, and cast into membranes following the same procedures as described above. The results of SEM image analysis of these membranes are presented in FIG. 1. The surface appearance of the membranes characterized by SEM were found to be very similar to that of Example 6 which was prepared by casting the MPP-DMP copolymer alone.

The blends of Examples 9-10 containing PS/PEO copolymer yielded membrane surfaces upon phase-inversion casting which had pore size distributions that showed as good or better consistency in pore size distribution as seen for Example 6, which was made from MPP-DMP copolymer alone (Table 6). From this we can conclude that the presence of short blocks of PS has not substantially disrupted the inherently good membrane-forming characteristics of the MPP-DMP copolymer. The contact angle of the membranes containing the PS-PEO diblock as additive show a slight trend towards reduced contact angle, and a decrease in Tg which most likely results from forming a miscible blend between the MPP-DMP copolymer and the PS blocks of the diblock copolymer. It is expected that this type of additive will not be soluble in NMP/water, contrary to PVP, and so it would be expected to be present in the membrane itself.

TABLE 6

Properties of Membranes Made from Blends of MPP-DMP Copolymer and PS/PEO Diblock Copolymer

| Ex. No. | Wt % Resin In NMP Casting Dope | Surface Pore Size Distribution of Membrane (μm) | Membrane Tg (° C.) |
|---|---|---|---|
| 6 | 16% Ex. 2 | 12.2 ± 3.8 | 210 |
| 9 | 16% Ex. 2 + 2% PS-PEO | 10.1 ± 2.0 | 183 |
| 10 | 16% Ex. 2 + 4% PS-PEO | 9.2 ± 1.7 | 176 |

Examples 18-20 and Comparative Example 3: Hollow Fiber Spinning

Figure 3:
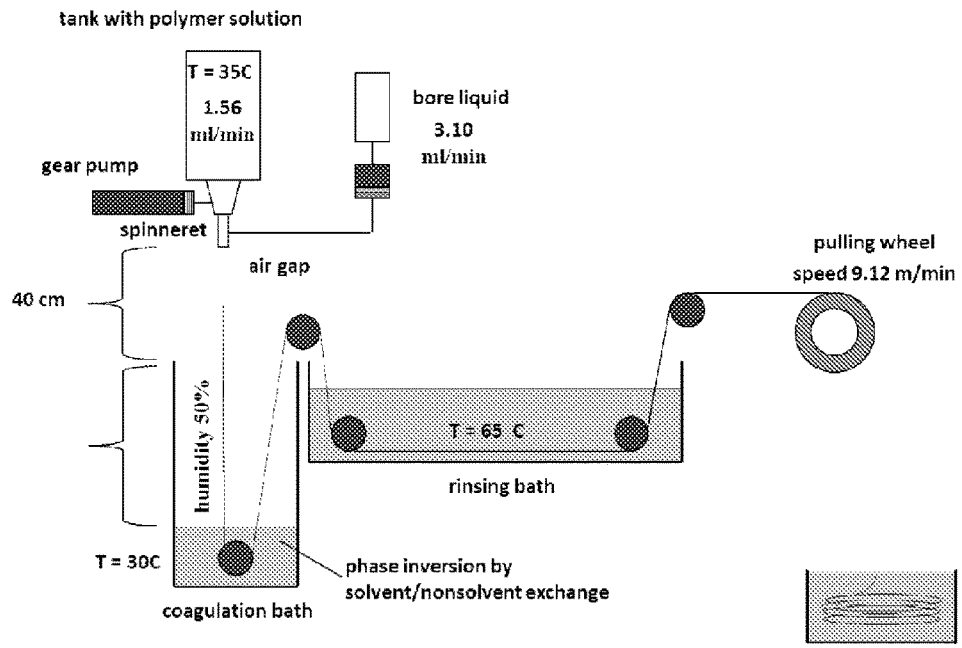
FIG. 3 depicts a diagram of a laboratory scale, dry-wet immersion precipitation hollow fiber spinning apparatus.

The membrane-forming compositions of Ex. 18-20, (containing the MPP-DMP copolymers of Ex. 11-13, respectively) and Comp. Ex. 3 (6020P, PVP K30, and PVP K90) were fabricated into hollow fiber membranes on a laboratory scale by dry-wet immersion precipitation spinning according to the method disclosed in WO2013/131848, using the apparatus shown in FIG. 3. ULTRASON™ E 6020P was maintained for 24 hr. under vacuum prior to mixing to remove all moisture. Mixing was done until homogenous solutions were obtained. The membrane-forming the composition was filtered through a 25-μm metal mesh to remove any residual particles in the composition and degassed for 24 hr. before use. A bore solution of 70 wt % deionized water and 30 wt % NMP was prepared and degassed for 24 hr. before use. The copolymer solution along with the bore liquid were simultaneously pumped through a double orifice spinneret and after passing the air gap, and immersed into the coagulation bath. The take-up velocity was controlled by a pulling wheel, which enabled also stretching of the fiber.

A summary of the fiber spinning conditions, spinneret geometry, and measured dimensions of the dried hollow fibers is shown in Table 10. For Comp. Ex. 3, the rinsing bath was held at 65° C. according to the example in the '848 application, which is understood to be for rinsing away excess PVP from the surface of the hollow fiber. For Examples 18-20, which were prepared from the 20/80, 50/50, and 80/20 MPP-PPE copolymers, respectively, the rinsing bath was held at 30° C. for safety in handling the fibers and because there is no PVP to be washed away. The take-up velocity was adjusted such that the wall thickness of the two hollow fiber samples was in the range of 40-60 micrometers. The post treatment process for the hollow fiber produced was as described in the '848 application. The fibers were washed in 70° C. purified water for 3 hr. After 1.5 hr, the water was exchanged. Afterwards the fibers were rinsed for another 24 hr. in water at tap temperature. After the rinsing step, the fibers were hung in the lab to dry in air at ambient temperature.

Based on the finding that the membrane-forming polymer solution viscosity in NMP was very sensitive to the amount of MPP co-monomer in the copolymer, the concentration of each resin was adjusted so as to yield an essentially constant solution viscosity of just over 3,000 cP. As a result there is a direct correlation between the level of MPP co-monomer in the copolymer and the mass of PPE per unit length of fiber, with E. 18 demonstrating the most efficient use of resin under the same spinning conditions. The fiber wall thickness was also maintained to a greater extent in Ex. 19, suggesting that with further optimization of fiber spinning conditions to reduce the wall thickness, a greater reduction in mass per unit length can be realized.

TABLE 10

Summary of Process Conditions for Hollow Fiber Spinning and Fiber Properties

| | Example | | | |
|---|---|---|---|---|
| | Comp. Ex. 3 | Ex. 18 | Ex. 19 | Ex. 20 |
| Wt % resin in NMP casting dope | 14% 6020P[a] | 18% Ex. 12 | 14% Ex. 11 | 20% Ex. 13 |
| Viscosity (cP at 35° C.) | | 3270 | 3091 | 3137 |
| Dope temp. [° C.] | 35 | 35 | 35 | 35 |
| Die temp. [° C.] | — | — | — | — |
| Shaft temp. [° C.] | ~22 | ~30 | ~30 | ~22 |
| Shaft humidity [%] | 50 | 60 | 60-65 | 60 |
| Room humidity [%] | 35 | 40 | 40 | 40 |
| $1^{st}$ bath temp. [° C.] | 30 | 30 | 30 | 30 |
| $2^{nd}$ bath temp. [° C.] | 65 | 30 | 30 | 30 |
| Air Gap [cm] | 100 | 100 | 100 | 100 |
| Dope extrusion rate [mL/min] | 1.56 | 1.56 | 1.56 | 1.56 |
| Bore extrusion rate [mL/min] | 3.1 | 3.1 | 3.1 | 3.1 |
| Take up velocity [m/min] | 9.12 | 7.04 | 7.07 | 7.00 |
| Spinneret dimensions | | | | |
| Inner diameter [mm] | 0.4 | 0.4 | 0.4 | 0.4 |
| Outer diameter [mm] | 1.12 | 1.12 | 1.12 | 1.12 |
| Dry hollow fiber dimensions by SEM | | | | |
| Inner diameter [μm] | 445 | 605 | 510 | 605 |
| Wall thickness [μm] | 59 | 41 | 47 | 23 |
| Mass per km (g) | 25.9 | 40.2 | 31.1 | 43.3 |

[a]Plus 5% PVP K30, 2% PVP K90, and 3% $H_2O$

SEM Comparison of Flat Sheet and Hollow Fiber Morphology

Figure 2:
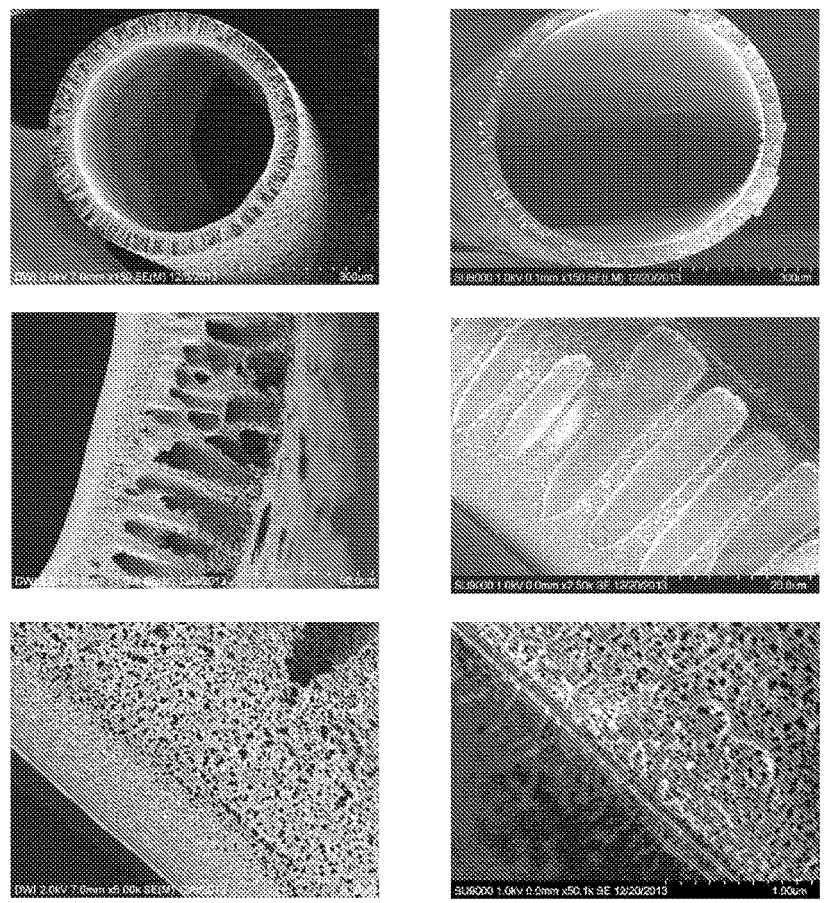
FIG. 2 depicts SEM images of the hollow fiber membranes of Comparative Example 3 and Example 18.

The hollow fibers of Comp. Ex. 3 and Ex. 18 were analyzed by SEM, the results of which are shown in FIG. 2. The hollow fibers of Comp. Ex. 3, prepared from PES/PVP, show a strongly asymmetric cross-sectional morphology, and similar to those obtained for flat membrane castings of the same dope composition. The dense selective layer appears to be thin for the PES/PVP membrane in both flat and the hollow fiber geometries. In comparison, the morphology of the hollow fiber of Ex. 18 shows a dense spongy morphology that persists across the fiber cross-section, which is also consistent with flat membranes produced from the same dope composition. Thus the poly(phenylene ether) copolymers disclosed herein provide membrane-forming characteristics that are superior to those of PES/PVP polymers in both flat and hollow fiber geometries.

The use of the terms "a" and "an" and "the" and similar referents in the context of describing the invention (especially in the context of the following claims) is to be construed to cover both the singular and the plural, unless otherwise indicated or clearly contradicted by context. "Or" means "and/or." The endpoints of all ranges directed to the same component or property are inclusive and independently combinable. Disclosure of a narrower range or more specific group in addition to a broader range is not a disclaimer of the broader range or larger group. The terms "first" and "second" and the like, as used herein do not denote any order, quantity, or importance, but are only used to distinguish one element from another. The term "comprises" as used herein is understood to encompass embodiments consisting essentially of, or consisting of, the named elements. Unless defined otherwise, technical and scientific terms used herein have the same meaning as is commonly understood by one of skill in the art to which this invention belongs. A "combination" is inclusive of blends, mixtures, alloys, reaction products, and the like.

As used herein, the term "hydrocarbyl" refers broadly to a moiety having an open valence, comprising carbon and hydrogen, optionally with 1 to 3 heteroatoms, for example, oxygen, nitrogen, halogen, silicon, sulfur, or a combination thereof. Unless indicated otherwise, the hydrocarbyl group can be unsubstituted or substituted, provided that the substitution does not significantly adversely affect synthesis, stability, or use of the compound. The term "substituted" as used herein means that at least one hydrogen on a hydrocarbyl group is replaced with another group (substituent) that contains a heteroatom selected from nitrogen, oxygen, sulfur, halogen, silicon, or a combination thereof, provided that the normal valence of any atom is not exceeded. For example, when the substituent is oxo (i.e. "=O"), then two hydrogens on a designated atom are replaced by the oxo group. Combinations of substituents and/or variables are permissible provided that the substitutions do not significantly adversely affect the synthesis, stability or use of the compound.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A separation module comprising a porous asymmetric membrane, comprising a poly(phenylene ether) copolymer comprising repeat units derived from 2,6-dimethylphenol and repeat units derived from 2-methyl-6-phenylphenol, and having an intrinsic viscosity of 0.7 to 1.5 deciliters per gram, measured in chloroform at 25° C. and a weight average molecular weight of 100,000 to 500,000 daltons, measured by gel permeation chromatography against polystyrene standards; and an amphiphilic block copolymer; wherein the porous asymmetric membrane is in a flat sheet, hollow fiber, capillary, or tubular configuration.

2. The separation module of claim 1, wherein the porous asymmetric membrane is a flat sheet wound into a spiral.

3. The separation module of claim 1, wherein the porous asymmetric membrane is a hollow fiber.

4. The separation module of claim 3, wherein the separation module comprises:
an enclosure configured to contain a bundle of the porous hollow fibers, the enclosure having an outlet configured for withdrawing a permeate fluid;
a first encasement comprising a thermoset or a thermoplastic polymeric material and located at a first end of the bundle, arranged such that the hollow fibers are embedded in the first encasement and communicate through the first encasement and are open on an outer face of the first encasement;
a second encasement comprising a thermoset or a thermoplastic polymeric material and located at a second end of the bundle opposite the first end of the bundle, arranged such that the hollow fibers are embedded in the second encasement and communicate through the second encasement and are open on an outer face of the second encasement;
a first end cap arranged and configured for attaching and sealing to the first end of the bundle or enclosure at or near the first encasement;
a second end cap arranged and configured for attaching and sealing to the second end of the bundle or enclosure at or near the second encasement;
an inlet for introducing a fluid mixture to be separated into bores of the hollow fibers at the first encasement; and
an outlet for withdrawing a retentate fluid from the bores of the hollow fibers at the second encasement.

5. A method of hemodialysis, the method comprising:
passing blood through the separation module of claim 1, such that the blood contacts a first side of the porous asymmetric membrane; and
passing a dialysis solution through the separation module such that the dialysis solution contacts a second opposite side of the porous asymmetric membrane to remove waste products from the blood.

6. A dialysis device for conducting liver dialysis on a patient suffering from liver failure, the device comprising the separation module of claim 1.

7. The dialysis device of claim 6, wherein the hollow fibers allow the passage of molecules having a molecular weight of up to 45 kilodaltons with a sieving coefficient of 0.1 to 1.0 in the presence of whole blood; wherein the dialysis device reduces the concentration of protein-bound toxins and inflammatory cytokines in the blood of the patient; wherein the dialysis device reduces the concentration of unconjugated bilirubin and bile acids in the blood of the patient; and wherein the dialysate passing the hollow fibers comprises from 1% to 25% human serum albumin.

8. A blood oxygenator comprising:
a housing;
a separation module comprising a plurality of the hollow fibers of claim 3 disposed within the housing for transporting a first fluid therethrough;
a first inlet in fluid communication with the hollow fibers for delivering the first fluid thereto;
a first outlet in fluid communication with the hollow fibers for receiving the first fluid therefrom; and
a second inlet and a second outlet in communication with regions disposed exterior to the hollow fibers.

9. A method of sugar purification, the method comprising:
passing a fluid comprising a combination of polysaccharides through the separation module of claim 1, such that the fluid contacts a first side of the porous asymmetric membrane; and
passing a polysaccharide through the porous asymmetric membrane to purify the sugar.

10. A method of protein or enzyme recovery comprising:
urging a fluid comprising a protein or enzyme through the separation module of claim 1, such that the fluid contacts a first side of the porous asymmetric membrane; and
removing a component from the fluid by passing the component through the porous asymmetric membrane to provide a retentate stream enriched in the protein or enzyme to recover the protein or enzyme.

11. A method of water purification comprising: passing a feedwater through the separation module of claim 1, such that the feedwater contacts a first side of the porous asymmetric membrane with a pressure greater than its osmotic pressure to produce purified water.

12. A water pretreatment system comprising the separation module of claim 1, designed for concentrating a feed and diluting a recirculating hypertonic solution to produce a slipstream; wherein the system comprises a water makeup element for receiving the slipstream and combining the slipstream with the hypertonic solution to provide solutes to the recirculating hypertonic solution; and wherein the recirculating hypertonic solution is suitable for desalination.

13. A method of pretreating water, the method comprising: receiving a feedwater; separating the feed water into a concentrator feed and a slipstream; processing the concentrator feed in a concentrator comprising the porous separation module of claim 1 to generate a hypertonic solution; combining the slipstream and the hypertonic solution to generate an effluent capable of decomposition into purified water and a recirculating hypertonic solution.

14. A system for separating water-insoluble oil from oil-containing wastewater, the system comprising the separation module of claim 1.

15. A method of wastewater treatment comprising treating an oil-containing wastewater with the system of claim 14.

16. An ultrafiltration device, the device comprising the separation module of claim 1, wherein the ultrafiltration device further comprises a filter housing comprising an inlet and an outlet, and a bundle of the tubular or capillary porous asymmetric membranes fitted in the filter housing, wherein the tubular or capillary porous asymmetric membranes are permanently hydrophilic, are open at a first inlet end and sealed at the other end, and are, at the first end, held in a membrane holder which closes off the space in between the tubular or capillary porous asymmetric membranes and the filter housing, and wherein the pore size of the tubular or capillary porous asymmetric membranes decreases in the direction of liquid flow.

17. An apparatus for purification of a liquid by membrane distillation comprising the separation module of claim 1, wherein the separation module further comprises a feed channel, a distillate channel, and a retentate channel, wherein the distillate channel and the retentate channel are separated by the porous asymmetric membrane.

18. The apparatus for purification of a liquid by membrane distillation of claim 17, further comprising: a segment comprising a first distribution chamber for a feed liquid to be supplied; a second distribution chamber located opposite the first distribution chamber for feed liquid to be discharged; a third distribution chamber for retentate stream to be supplied; and a fourth distribution chamber opposite the third the third distribution chamber for the retentate stream to be discharged, wherein: the segment is provided with a first pump for pumping the feed stream pressure into the segment and a second pump which is arranged downstream the second distribution chamber for pumping the retentate stream under pressure into the retentate channel; the wall between the feed channel and the distillate channel comprises a condenser surface in the form of a non-porous membrane; the wall between the retentate channel and the distillate channel comprises the porous asymmetric membrane; and inside the retentate channel a further channel is arranged for allowing a fluid stream to be brought into heat transfer contact with the retentate stream.

19. The separation module of claim 1, wherein the amphiphilic block copolymer comprises a hydrophilic block of poly(ethylene oxide).

20. The separation module of claim 1, wherein the porous asymmetric membrane further comprises a block copolymer of poly(ethylene oxide) and poly(propylene oxide).

* * * * *